US011300451B2

(12) United States Patent
Matousek et al.

(10) Patent No.: US 11,300,451 B2
(45) Date of Patent: Apr. 12, 2022

(54) RAMAN SPECTROMETER

(71) Applicant: United Kingdom Research and Innovation, Swindon (GB)

(72) Inventors: Pavel Matousek, Oxfordshire (GB); Kay Sowoidnich, Werder (DE); Michael Towrie, Oxfordshire (GB)

(73) Assignee: UNITED KINGDOM RESEARCH AND INNOVATION, Swindon (GB)

( * ) Notice: Subject to any disclaimer, the term of this patent is extended or adjusted under 35 U.S.C. 154(b) by 0 days.

(21) Appl. No.: 17/282,438

(22) PCT Filed: Oct. 4, 2019

(86) PCT No.: PCT/GB2019/052808
§ 371 (c)(1),
(2) Date: Apr. 2, 2021

(87) PCT Pub. No.: WO2020/070514
PCT Pub. Date: Apr. 9, 2020

(65) Prior Publication Data
US 2021/0389180 A1    Dec. 16, 2021

(30) Foreign Application Priority Data
Oct. 5, 2018    (GB) ..................... 1816285

(51) Int. Cl.
*G01J 3/44*        (2006.01)
*G01J 3/02*        (2006.01)
(Continued)

(52) U.S. Cl.
CPC .............. *G01J 3/44* (2013.01); *G01J 3/0208* (2013.01); *G01J 3/0262* (2013.01);
(Continued)

(58) Field of Classification Search
CPC .......... G01J 3/44; G01J 3/0208; G01J 3/0262; G01J 3/2803; G01J 2003/4424;
(Continued)

(56) References Cited

U.S. PATENT DOCUMENTS

| 5,141,609 A | 8/1992 | Sweedler et al. |
| 5,838,372 A | 11/1998 | Wood |

(Continued)

FOREIGN PATENT DOCUMENTS

| DE | 102007000988 A1 | 5/2009 |
| DE | 102007000988 B4 | 6/2014 |

(Continued)

OTHER PUBLICATIONS

Barman I. et al., "Effect of photobleaching on calibration model development in biological Raman spectroscopy" Journal of Biomedical Optics 2011, 16 (1), pp. 011004-1-011004-10.

(Continued)

*Primary Examiner* — Abdullahi Nur
(74) *Attorney, Agent, or Firm* — Lempia Summerfield Katz LLC

(57) ABSTRACT

There are disclosed methods and apparatus (10) for measuring Raman spectral features (52) of a sample (12), from which background light of variable intensity is also received, for example due to the incidence of ambient light (14) or due to variable fluorescence. Detection pixels (42) and storage pixels (44) are defined on a CCD device (40). Laser probe light (22) is directed to the sample. In a repeated cycle of first and second intervals, in each first interval background light is received at detection pixels, and in each second interval both background light and scattered laser probe light is received at the detection pixels. The accumulated signal from each of the first and second intervals is retained in the storage pixels during the second and first (Continued)

intervals respectively. In other aspects laser probe light is directed to the sample during both of the first and second intervals, but has a different wavelength in each interval.

43 Claims, 13 Drawing Sheets

(51) Int. Cl.
     *G01J 3/28* (2006.01)
     *G01N 21/65* (2006.01)
     *H04N 5/372* (2011.01)

(52) U.S. Cl.
     CPC ............ *G01J 3/2803* (2013.01); *G01N 21/65* (2013.01); *H04N 5/372* (2013.01); *G01J 2003/4424* (2013.01); *G01N 2201/06113* (2013.01)

(58) Field of Classification Search
     CPC .......... G01J 3/0218; G01J 3/10; G01J 3/0289; G01J 3/28; G01N 21/65; G01N 2201/06113; H04N 5/372; A61B 2560/0431; A61B 2562/0233; A61B 5/7203; A61B 5/0075
     See application file for complete search history.

(56) References Cited

U.S. PATENT DOCUMENTS

| | | | |
|---|---|---|---|
| 7,940,377 B1 | 5/2011 | Schmitt et al. | |
| 8,179,526 B2 | 5/2012 | Bennett et al. | |
| 8,570,507 B1 | 10/2013 | Cooper et al. | |
| 2005/0254047 A1 | 11/2005 | Brady et al. | |
| 2006/0197947 A1 | 9/2006 | Wang et al. | |
| 2007/0222982 A1 | 9/2007 | Tuschel et al. | |
| 2013/0265295 A1* | 10/2013 | Ogawa | G09G 3/36 345/214 |
| 2016/0356647 A1 | 12/2016 | Wiegand et al. | |

FOREIGN PATENT DOCUMENTS

| | | |
|---|---|---|
| DE | 102016111747 A1 | 12/2017 |
| EP | 2806263 A1 | 11/2014 |
| WO | 03062798 A1 | 7/2003 |
| WO | 2006061565 A1 | 6/2006 |
| WO | 2006061566 A1 | 6/2006 |
| WO | 2007112099 A2 | 10/2007 |
| WO | 2007113566 A2 | 10/2007 |
| WO | 2011033017 A1 | 3/2011 |

OTHER PUBLICATIONS

Barone G. et al. "Nondestructive investigation on the 17-18th centuries Sicilian jewelry collection at the Messina regional museum using mobile Raman equipment", Journal of Raman Spectroscopy, 2015, 46, pp. 989-995 https://doi.org/10.1002/jrs.4649.
Carter J. C. et al., "Standoff Detection of High Explosive Materials at 50 Meters in Ambient Light Conditions Using a Small Raman Instrument" Applied Spectroscopy 2005, 59 (6) pp. 769-775.
Cletus B. et al., "Real-Time Detection of Concealed Chemical Hazards under Ambient Light Conditions Using Raman Spectroscopy" Journal of Forensic Sciences, 2013, 58, pp. 1008-1014.
De Luca A. C. et al., "Online Fluorescence Suppression in Modulated Raman Spectroscopy" Anal. Chem. 2010, 82, pp. 738-745.
Desroches J. et al., "Characterization of a Raman Spectroscopy Probe System for Intraoperative Brain Tissue Classification" Biomedical Optics Express 2015, 6 pp. 2380-2397.
Desroches J. et al., "Raman Spectroscopy in Microsurgery: Impact of Operating Microscopy Illumination Sources on Data Quality and Tissue Classification" Analyst 2017, 142, pp. 1185-1191.
Dochow S. et al., "Etaloning, Fluorescence and Ambient Light Suppression by Modulated Wavelength Raman Spectroscopy" Biomedical Spectroscopy and Imaging, 2012, 1, pp. 383-389.
GB Search Report in GB Application No. 1816285.9, dated Apr. 1, 2019, 1 page.
Heming R. et al., "Optical CCD lock-in device for Raman difference spectroscopy" DGaO Proceedings 2008 http://www.dgao-proceedings.de—ISSN: 1614-8436.
Hernanz A. et al., "Spectroscopic characterisation of crusts interstratified with prehistoric paintings preserved in open-air rock art shelters", Journal of Raman Spectroscopy, 2014, 45, pp. 1236-1243.
Hopkins A. J. et al., "Portable Deep-Ultraviolet (DUV) Raman for Standoff Detection" Applied Spectroscopy 2016, 70 (5), pp. 861-873.
International Search Report and Written Opinion of the International Searching Authority in PCT/GB2019/052808, dated May 24, 2020, 16 pages.
Izake E. L. "Forensic and Homeland Security Applications of Modern Portable Raman Spectroscopy" Forensic Science International, 2010, 202, pp. 1-8.
Jermyn M. et al., "Neural Networks Improve Brain Cancer Detection with Raman Spectroscopy in the presence of Operating Room Light Artifacts" Journal of Biomedical Optics 2016, 21, pp. 094002-1-094002-6.
Maiwald M. et al., "A Portable Shifted Excitation Raman Difference Spectroscopy System: Device and Field Demonstration" Journal of Raman Spectroscopy 2016, 47, pp. 1180-1184.
Maiwald M. et al., "Shifted Excitation Raman Difference Spectroscopy using a Dual-Wavelength DBR Diode Laser at 671nm" Proc. SPIE 8935, Advanced Biomedical and Clinical Dianostic Systems X11, 2014, 8935, pp. 89350M-1-89350M-8.
Matousek et al., "Simple Reconstruction Algorithm for Shifted Excitation Raman Difference Spectroscopy" Applied Spectroscopy, 2005, 59, pp. 848-851.
Mihály J. et al., "FTIR and FT-Raman Spectroscopic Study on Polymer Based High Pressure Digestion Vessels" Croatica Chemica Acta 2006, 79, p. 497-501.
Povel H. et al., "Charge-coupled device image sensor as a demodulator in a 2-D polarimeter with a piezoelastic modulator" Applied Optics, 1990, 29 (8), pp. 1186-1190.
Povel H. P. et al., "Two-dimensional Polarimeter with a Charge-Coupled-Device Image Sensor and a Piezoelastic Modulator" Applied Optics 1994, 33, pp. 4254-4260.
Qi J. et al., "Automated Image Curvature Assessment and Correction for High-Throughput Raman Spectroscopy and Microscopy" Biomedical Spectroscopy and Imaging 2014, 3, pp. 359-368.
Ravindran T. R. et al., "On- and off-site Raman study of rock-shelter paintings at worid-heritage site of Bhimbetka" Journal of Raman Spectroscopy, 2013, 44, pp. 108-113.
Rodriguez et al., "Quantitative Evaluation of the Sensitivity of Library-Based Raman Spectral Correlation Methods", Analytical Chemistry 2011, 83, pp. 4061-4067.
Scheier R. et al., "Early Postmortem Prediction of Meat Quality Traits of Porcine Semimembranosus Muscles Using a Portable Raman System" Food and Bioprocess Technology 2014, 7, pp. 2732-2741.
Shimada R. et al., "Parallelized shifted-excitation Raman difference spectroscopy for fluorescence rejection in a temporary varying system" Journal of Biophotonics DOI: 10.1002/jbio.201960028 2019, pp. 1-10.
Spirig T. et al., "The Lock-In CCD—Two Dimensional Synchronous Detection of Light", IEEE Journal of Quantum Electronics, 1995, 31 (9), pp. 1705-1708.
Van de Voorde L. et al, "Study of a unique 16th century Antwerp majolica floor in the Rameyenhof castle's chapel by means of X-ray fluorescence and portable Raman analytical instrumentation", Spectrochimica Acta Part B: , 2014, 102, pp. 28-35.
Vandenabeele P. et al. "The role of mobile instrumentation in novel applications of Raman spectroscopy: archaeometry, geosciences, and forensics" Chemical Society Reviews 2014, 43, pp. 2628-2649 DOI: 10.1039/c3cs60263j.

(56) References Cited

OTHER PUBLICATIONS

Zhao J. et al., "Clinical Raman Measurements under Special Ambient Lighting Illumination" Journal of Biomedical Optics, 2014, 19 (11), pp. 111609-1-111609-4.
International Search Report and Written Opinion of the International Searching Authority in PCT/GB2019/052808, dated Mar. 24, 2020, 16 pages.

* cited by examiner

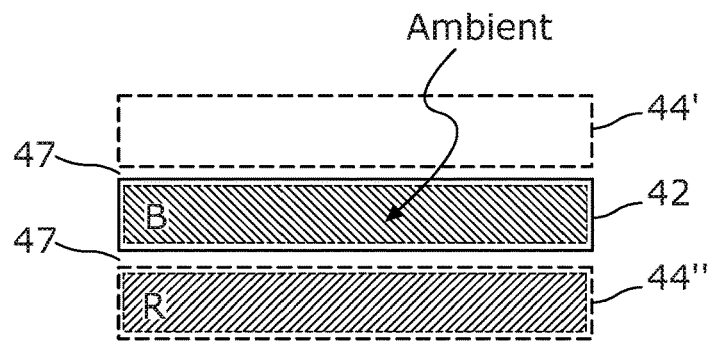
FIGURE 2a(i)
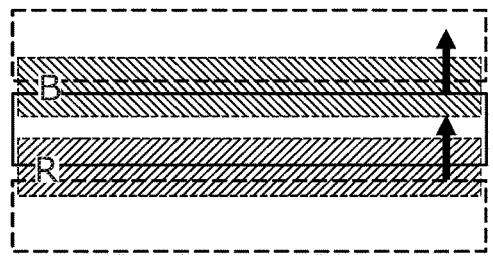
FIGURE 2a(ii)
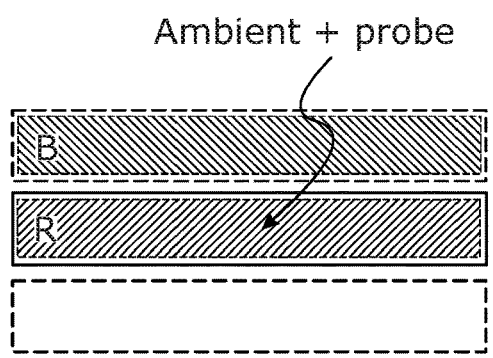
FIGURE 2a(iii)
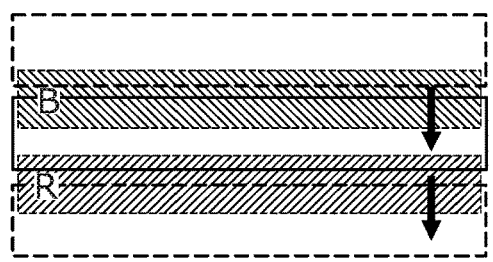
FIGURE 2a(iv)

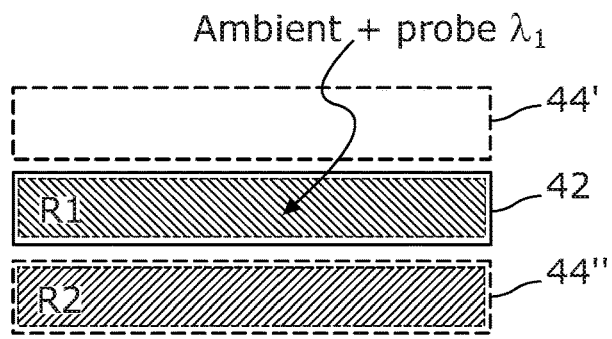
FIGURE 2b(i)
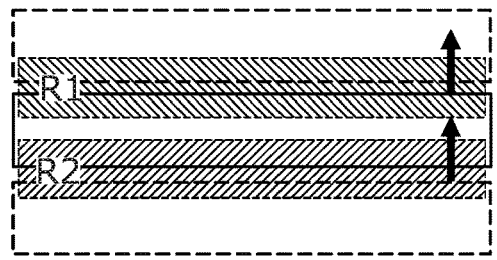
FIGURE 2b(ii)
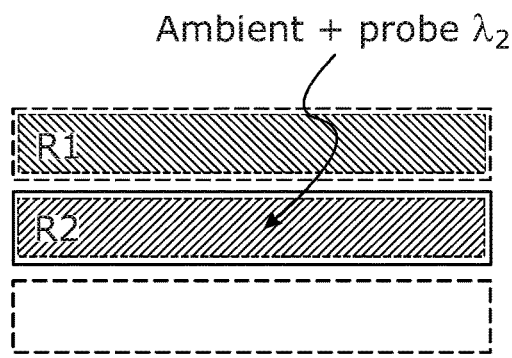
FIGURE 2b(iii)
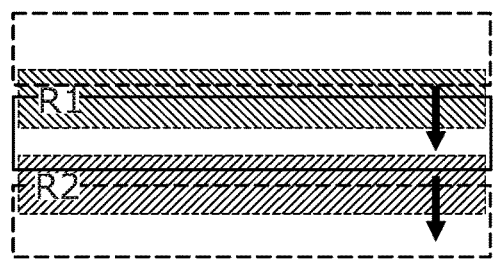
FIGURE 2b(iv)

RAMAN SPECTROMETER

RELATED APPLICATIONS

The present patent document is a § 371 nationalization of PCT Application Serial No. PCT/GB2019/052808, filed Oct. 4, 2019, designating the United States, which is hereby incorporated by reference, and this patent document also claims the benefit of United Kingdom Application No. GB 1816285.9, filed Oct. 5, 2018, which are also hereby incorporated by reference.

The present invention relates to methods and apparatus for measuring one or more Raman spectral features of a sample. For example, embodiments of the invention may be useful for implementation in hand held apparatus for carrying out Raman spectroscopy on a sample, for example for use away from the laboratory.

INTRODUCTION

Raman spectroscopy is a powerful analytical method which can be used to determine the chemical composition of various samples. The technique has a wide range of applications including material characterization, explosives detection, food analysis, pharmaceutical analysis, medical diagnosis, forensics, cultural heritage and extra-terrestrial sample investigation in space missions to name but a few. Techniques to provide accurate and effective Raman spectral analysis in the controlled environment of the laboratory are well developed.

However, in more practical areas of application outside of the laboratory, providing a robust instrument for Raman spectral analysis and characterisation of samples presents many challenges, such as how to provide sufficiently rapid detection of materials given the very low cross sections of Raman scattering compared to other scattering and emission types and photon signals in general, how to provide a sufficiently lightweight and portable yet robust device, how to avoid adverse environments effects such as vibration and contamination, and so forth.

Raman spectroscopy of a sample can also be adversely affected by fluorescence of the sample, and in particular by fluorescence excited by the same laser light illumination of the sample as used for the detection of Raman spectral features.

The invention seeks to address problems and limitations of the related prior art.

SUMMARY OF THE INVENTION

The inventors have noted that, due to the very weak nature of Raman spectral signals, Raman spectral analysis is very susceptible to ambient light interference, which can easily overwhelm the Raman scattering signal. Such ambient light may be characterised as light falling on the sample which is not specifically intended for determining Raman spectral features of the sample, for example direct or indirect sunlight, and artificial light sources such as room and desk lights. In particular, such ambient light does not include laser probe light directed to the sample for the purposes of detecting Raman spectral features characterising the sample, but may for example include all other light incident on the sample.

Applications of Raman spectroscopy outside the usual laboratory environment may therefore be compromised by undesired sources of light (such as artificial light or daylight) which may also be subject to additional background movement/variations (e.g. due to shadow casting by moving objects, instrument or personnel movements, light spectral intensity fluctuations and so forth).

Ambient light can often be prevented from entering the Raman instrument by physically covering the contact area between a sample and an instrument probe head. However, this is not always practical or feasible, particularly if a robust and user friendly, portable Raman analyser is needed. It might be possible to overcome interference from ambient light using solutions such as the use of short-pulsed lasers in conjunction with gating, but this technique implies high peak powers which could damage sensitive samples, and instrumental complexity inherent to this approach might also interfere with the goal of producing small lightweight (e.g. handheld) devices at reasonable cost.

Another approach could be to use laser probe light in the ultraviolet spectral range below 300 nm, since solar radiation is blocked in this region due to atmospheric ozone absorption, but this could result in sample degradation due to the UV radiation, and other sources of ambient light apart from sunlight may remain a problem. This use of the UV region can also restrict the use of some special Raman modalities such as Spatially Offset Raman Spectroscopy (SORS) or transmission Raman spectroscopy for probing deep inside turbid samples which relies on non-absorbance of the matrix that may not often be achievable in this spectral region.

The effects of ambient light incident on a sample are likely to be more difficult to compensate for when the incident ambient light varies in intensity and/or spectral content, especially where these variations are on the same time scale as, or more rapid than a single exposure or acquisition period for a Raman spectrum.

The inventors have therefore sought to address the detrimental effect of rapid and irregular variations of ambient light using a quasi-simultaneous acquisition of spectra resulting both from illumination by laser probe light and ambient light at the same time, and resulting from ambient light illumination alone, using a technique based on fast optical lock-in detection using a charge-shifting operation in a charge coupled device (CCD), with charge retention on the CCD chip.

The described techniques can also be used to help compensate for variations in the levels of fluorescence emitted by a sample during the time taken to measure Raman spectral features. Such variations may for example be due to photobleaching in which the fluorescence signal reduces appreciably over time. Such photobleaching may in particular take place due to illumination by the laser beam used for acquiring the Raman spectral features. Various mechanisms can be involved in such photobleaching, for example the deactivation of excited-state fluorophores on contact with other molecules in the sample.

Due to read-out and analogue-to-digital conversion steps required for each recorded spectrum, as well as typical low Raman signal strengths, there is a fundamental technical limitation of conventional CCD based detectors practically limiting the operation speed to less than about 10 Hz. To enable the rapid alternating detection of spectra resulting from laser probe light containing the desired Raman spectral features with spectra resulting only from ambient light, the invention therefore seeks to exploit a CCD charge-shifting technique. In this approach, CCD read-out and digitization steps, which slow down the acquisition and introduce additional (read-out) noise to the data, are only performed once after many (for example thousands of) cycles of Raman and background spectral signal accumulation. Briefly, for one cycle of a much longer overall exposure period a specific area of the CCD is exposed to collected light containing both the laser probe light and ambient light scattered from a sample.

In the same cycle the accumulated charge is shifted to an non-illuminated area (e.g. above the active illumination area) by shifting the entire charge on CCD chip by a certain number of rows, n, in one direction and the previously illuminated area on the CCD chip is now exposed to ambient light contributions only acquired by switching off or blocking the laser excitation source before the sample. The cycle then continues with another shift of the entire charge by n rows in reverse presenting the previously acquired charge with Raman signal back into the active illumination area and starting another Raman exposure whilst the previously acquired background is transferred into another non-illuminated area, e.g. below the active illumination area. This cycle is then repeated for the duration of an exposure period which could for example be a fixed or predetermined period or be until sufficient charge is built up for it to be read or CCD saturation level is approached.

Due to the absence of any digitization or other readout from the CCD within the cycles of a single exposure period, and the involvement of only charge movement up and down on the CCD chip, the charge shifting periods can be facilitated at frequencies in the kilohertz range with practically no noise penalty on shifted charge, which can be kept accumulating within the CCD pixels throughout the entire exposure period. In this way, the charges accumulated during many, for example several thousand, cycles will permit the retrieval of spectra with improved high signal-to-noise ratio. The final readout of spectral signals from the CCD will only introduce read out noise once to the spectra which, given the charge signal height at that stage, can be considered negligible.

The above technique can also be implemented where a cycle includes accumulation of charge due to laser excitation of a first wavelength, shifting of that charge to a non-illuminated area, and then accumulation of charge due to laser excitation of a second wavelength, in both cases with the sample also being exposed to ambient light, with the spectra due to the two different excitation wavelengths then being combined in a process which largely removes the contribution of the ambient light.

In particular, the invention provides methods of measuring Raman spectral features of a sample from which background light is also received, in particular when that background light is expected to be variable, for example variable in terms of intensity and/or spectral content, and perhaps also polarisation properties. Detection pixels and storage pixels are defined on a charge coupled device (CCD) having a plurality of pixels, and a laser light source arranged to direct laser probe light to the sample is provided. Collection optics arranged to direct light from the sample to the detection pixels is also provided. For example, light from the sample and collected by the collection optics may include components of ambient light incident on the sample which are then scattered in a wide variety of ways, including by both elastic and inelastic scattering mechanisms, by diffuse and specular reflection, and scattering both at and beneath the surface of the sample.

Light from the sample may also or instead include other components such as components of fluorescence emitted from the sample, for example following excitation by the laser probe light directed to the sample for the purposes of determining the Raman spectral features. Such fluorescence may be variable for example due to processes such as photobleaching, and compensation of such variations can be achieved using the invention in the same way as the invention is able to compensate for variations in ambient light.

In a first aspect the method comprises, for the duration of an exposure period, repeating a cycle of at least a first interval during which background light from the sample, but not laser probe light, is received at the detection pixels for the accumulation of first, background, spectral signals at those pixels, and a second interval during which both background light from the sample and laser probe light scattered by the sample, and in particular such light that has been Raman scattered by the sample, is received at the detection pixels for the accumulation of second, Raman, spectral signals at those pixels. In particular, the background light from the sample may be or may comprise ambient light scattered by the sample, but may be taken not to include elements of the laser probe light which have been elastically or inelastically scattered, particularly at the sample.

During the first intervals, the first, background, spectral signals are accumulated in the detection pixels due to incidence of the ambient light, while storing the accumulated second, Raman, spectral signals in said storage pixels. During the second intervals, the second, Raman, spectral signals are accumulated in the detection pixels due to incidence of both the background light and laser probe light, while storing the accumulated first, background, spectral signals in said storage pixels. The accumulated second, Raman, spectral signals therefore include contributions from both the scattered laser probe light and the background light received at the detection pixels during the second intervals, while the accumulated first, background, spectral signals include only contributions from the background.

In the first aspect, the wavelength of the laser probe light is held constant during an exposure period, although the laser light source is switched off or the probe light blocked from reaching the sample at least during the first intervals.

In a second aspect, more than one wavelength of laser probe light is used, in particular a first wavelength is used during each first interval, and a second wavelength different to the first wavelength is used during each second interval. These first and second wavelengths should each be held constant for a single exposure period, and typically may also be held constant over multiple exposure periods.

In the second aspect, the method comprises, for the duration of an exposure period, repeating a cycle of at least a first interval during which both background light from the sample, and laser probe light of a first wavelength which is then scattered by the sample, and in particular such light that has been Raman scattered by the sample, are received at the detection pixels for the accumulation of first, Raman, spectral signals at those pixels, and a second interval during which both background light from the sample and laser probe light of a second wavelength which is then scattered by the sample, and in particular such light that has been Raman scattered by the sample, the second wavelength being different to the first wavelength, are received at the detection pixels for the accumulation of second, Raman, spectral signals at those pixels.

In particular, the background light from the sample may be or may comprise ambient light scattered by the sample, and/or may be or may comprise fluorescence of the sample. However the background light may be taken not to include elements of the laser probe light which has been elastically or inelastically scattered, particularly at the sample. For example, such fluorescence of the sample may be excited at least in part by the laser probe light incident on the sample, and may be subject to diminishment in intensity over time due to photobleaching of the sample in particular by the same laser light.

During the first intervals, the first, Raman spectral signals are further accumulated in the detection pixels, while storing the accumulated second, Raman spectral signals in said storage pixels. During the second intervals, the second, Raman spectral signals are accumulated in the detection pixels, while storing the accumulated first, Raman spectral signals in said storage pixels.

In either of the above aspects, after the exposure period, the first (background or Raman) spectral signals and the second (Raman) spectral signals accumulated during the exposure period can be read from the CCD, for example including digitisation, electron multiplication, spatial averaging or binning, and other techniques as required.

Compensated Raman spectral signals from which signals due to the background light have largely been removed, can then be calculated using the read first and second spectral signals from one or more such exposure periods. One or more chemical characteristic of the sample can then be determined from the compensated Raman spectral signals from one or more exposure periods, such as an identification and/or concentration of one or more chemical species present at or in the sample.

The compensated spectral signals can be calculated in various ways from the available spectral signals. In the first aspect, the first, background, spectral signals can simply be subtracted from the second, Raman, spectral signals. In the second aspect, calculation of the compensated spectral signals may sometimes be more involved, but some suitable techniques are described below and for example in U.S. Pat. No. 8,570,507.

For the first aspect, the laser probe light may be incident on the sample during each second interval and be absent from the sample during each first interval, for example by operating the laser light source to emit said laser probe light only during each said second interval, and not during each first interval. Furthermore, guard periods may be provided within the second interval when the laser light source does not emit laser light to reduce the chances of contamination of the background spectral signals.

For the second aspect, the laser light source may be operated to emit only the first wavelength during the first interval, and only the second wavelength during the second interval. A single laser which is operated at at least two different wavelengths may be used, or multiple lasers each operating at different wavelengths may be comprised in the laser light source.

In some implementations of the second aspect, a third interval can be included in the cycle in which only background light from the sample is received at the detector pixels, so as to accumulate third, background, spectral signals. These third spectral signals are stored in the storage pixels during the first and second intervals. At the end of an exposure period all three spectral signals are read out. Compensated spectral signals are then calculated using all three of the first and second, Raman, spectral signals, and the third, background spectral signals, for further improved removal of background light signals (which may include fluorescence signals for the first two intervals) from the compensated Raman spectral signals.

Each exposure period may comprise for example at least 10, or at least 100, or at least 1000 of each of the first and second intervals, and third and further intervals if also used. If a combination of a first and second interval (and optionally one or more further intervals) is a cycle, then such a cycle may repeat for example at a frequency of between 300 Hz and 3 kHz. The lengths and distributions of the first and second intervals may be the same in each cycle of an exposure period, but this is not essential and varying lengths and combinations, regular or irregular may be used, as long as the different intervals are sufficiently interleaved within the exposure period to provide the required level of interleaving between the different intervals to adequately compensate the Raman spectral signals for background light having a given or expected level of variation.

The duration of an exposure period may be chosen or preselected according to the expected time required to acquire a Raman spectral signal of sufficient signal to noise ratio to determine target characteristics of the sample at a sufficient level of accuracy, and may be preset in the apparatus or could be determined by the apparatus as required for example to meet target performance levels. Typically, each exposure period may have a duration of at least 0.1 seconds, or at least one second.

The collection optics may comprise a spectrometer arranged to spectrally disperse the light scattered from the sample across the detection pixels, to thereby form a spatially dispersed spectrum.

Some or all of the described methods may be carried out by a hand held device. For example, a hand held device may be provided to carry out just the generation, delivery and collection of probe light and acquisition of the spectral signals which are then passed to another device or computer system for further analysis and display, or the hand held device may also provide analysis of the spectra and display of characteristics of the sample determined from the spectra.

The repeated cycle may further comprise a further interval during which collected light having different properties, for example comprising laser probe light having been scattered by a reference sample, is received at the detection pixels for the accumulation of further or other spectral signals such as reference spectral signals. This may enable the Raman spectral signals to be more accurately analysed, for example using a spectral differencing technique with the reference spectral signals.

The spectral signals may be moved between the detection pixels and the storage pixels by row shifting charge contents of the pixels of the CCD. Where we refer to rows in this document, this is intended to refer to one dimensional arrays of pixels on the CCD which can be shifted as a whole along a dimension perpendicular to the dimension of the extended array, and whether this is usually referred to in the context of a particular CCD type as a "row" or by some other term. The perpendicular dimension may also typically be the dimension along which the CCD pixels are read in a read out operation, but this does not have to be the case.

The storage pixels may be provided by at least first and second groups, for example contiguous blocks, of storage pixels disposed on opposing sides of detection pixels which may also be provided as a contiguous block, the first group being used for storage of the accumulated first, background or Raman, signals, and the second group being used for storage of the accumulated second, Raman, spectral signals. Further storage pixel groups may be provided for third or further spectral signals.

If the storage pixels comprise at least first and second groups of storage pixels disposed on opposing sides of the detection pixels, then the method can comprise: during a first exposure period the first group being used for storage of the accumulated first, background or Raman, spectral signals, and the second group being used for storage of the accumulated second, Raman, spectral signals; and during a second exposure period the first group being used for storage of the accumulated second, Raman, spectral signals, and the second group being used for storage of the accumulated first, background or Raman, spectral signals. In this way, asymmetries between the two blocks of storage pixels, or between movement of spectral signals into and out of the two blocks, can be more easily compensated for in subsequent analysis, for example by combining the results of the first and second exposure periods. One cause of such asymmetry could be asymmetric projection of the collected light onto the detection pixels.

To this end, the method may also comprise reading the accumulated first and second spectral signals from the CCD at the end of each of the first and second exposure periods; combining together the accumulated first spectral signals from both exposure periods; combining together the accumulated second spectral signals from both exposure periods; and calculating compensated Raman spectral signals using the combined first and second spectral signals from both exposure periods.

The storage pixels may comprise rows or blocks or rows of pixels interleaved between rows or blocks of rows of the detection pixels. Although such interleaving can reduce the distance over which spectral signals need to be row shifted on the CCD between intervals, and can reduce the amount of storage pixel space required, it may lead to a requirement to provide masking which is arranged to block light scattered from the sample from being received at the storage pixels.

The laser light source may be arranged to direct laser probe light to an illumination region on a surface of the sample, and the collection optics may be arranged to direct light scattered from a collection region on the sample surface. Either or both of these illumination and collection regions may be fixed or movable. In some embodiments the collection region may be spatially offset from the illumination region, and in some embodiments the offset may be controlled for example in order to carry out spatially offset Raman spectroscopy so as to determine one or more subsurface characteristics of the sample, optionally as a function of depth into the sample. Either or both of the illumination region and collection region on the sample surface may be continuous or made up of multiple separated sub-regions. Although the entry and collection regions may typically be circular or elliptical, they may take a variety of other shapes and configurations.

In particular, the method may comprise accumulating both first, background or Raman, spectral signals and second, Raman, spectral signals during each of a plurality of exposure periods, but using a spatial offset between said illumination and collection regions which is different for each of the exposure periods. One or more compensated Raman spectral features or one or more chemical characteristics related to those spectral features can then be determined for one or more subsurface regions of the sample, by associating the first spectral signals and second spectral signals for each offset with a different depth or distribution of depth within the sample.

The invention also provides apparatus corresponding to and arranged to implement various aspects of the described methods. For example, in association with the above first aspect the invention provides apparatus for detecting Raman spectral features of a sample from which background light is also received, for example under conditions of variable ambient light, comprising: a charge coupled device (CCD) having a plurality of pixels, the pixels comprising detection pixels and storage pixels; a laser light source arranged to direct laser probe light to the sample; collection optics arranged to direct light scattered from the sample to the detection pixels; and a controller arranged to implement an exposure period during which are interleaved a plurality of first intervals when background light from the sample, but not laser probe light, is received at the detection pixels for the accumulation of first, background, spectral signals at those pixels, and a plurality of second intervals during which both background light from the sample and laser probe light scattered by the sample is received at the detection pixels for the accumulation of second, Raman, spectral signals at those pixels, such that during each first interval, the first, background, spectral signals are further accumulated in the detection pixels, while storing the accumulated second, Raman, spectral signals in said storage pixels, and such that during each second interval, the second, Raman, spectral signals are further accumulated in the detection pixels, while storing the accumulated first, background, spectral signals in said storage pixels. In particular, the background light from the sample may be or may comprise ambient light scattered by the sample.

In particular, in this first aspect the laser light source may emit laser probe light during the second intervals, but not during the first intervals.

In association with the second aspect above, the invention provides apparatus for detecting Raman spectral features of a sample from which background light is received, for example under conditions of variable ambient light and/or variable fluorescence, comprising: a charge coupled device (CCD) having a plurality of pixels, the pixels comprising detection pixels and storage pixels; a laser light source arranged to direct laser probe light of either a first or a second wavelength to the sample; collection optics arranged to direct light scattered from the sample to the detection pixels; a controller arranged to implement an exposure period during which are interleaved a plurality of first intervals during which both background light from the sample, and laser probe light of the first wavelength scattered by the sample, are received at the detection pixels for the accumulation of first, Raman, spectral signals at those pixels, and a plurality of second intervals during which both background light from the sample and laser probe light of the second wavelength scattered by the sample are received at the detection pixels for the accumulation of second, Raman, spectral signals at those pixels.

In particular, the background light from the sample may be or may comprise ambient light scattered by the sample, and/or may be or may comprise fluorescence of the sample. For example, such fluorescence of the sample may be caused at least in part by the laser probe light incident on the sample, and may be subject to diminishment in intensity over time due to resulting photobleaching of the sample.

In this second aspect the apparatus is arranged such that, during the first intervals, the first, Raman spectral signals are further accumulated in the detection pixels, while the accumulated second, Raman, spectral signals are stored in said storage pixels, and such that during the second intervals, the second, Raman, spectral signals are accumulated in the detection pixels, while the accumulated first, Raman, spectral signals are stored in the storage pixels.

In this second aspect the laser light source may emit laser probe light of the first wavelength during the first intervals, and emit laser probe light of the second wavelength during the second intervals. This may be implemented for example using a single, switchable wavelength laser, or multiple lasers each arranged to emit a different wavelength.

In either aspect, the apparatus may further comprise an analyser arranged to receive from the CCD, after an exposure period, the first and second spectral signals accumulated during the exposure period, and to calculate compensated Raman spectral signals from the accumulated spectral signals, compensated to remove some or essentially all of the signal due to the background light. Such an analyser may be arranged to output a characteristic of the sample determined from the compensated Raman spectral signals.

In particular, the apparatus may be a hand-held or portable device, for example suitable for use by security, military, industrial or other personnel working in environments such as airports, factories, in the field, and so forth.

The collection optics may comprise a spectrometer arranged to spectrally disperse the light scattered from the sample across the detection pixels.

In experiments using polytetrafluoroethylene (PTFE) as a sample material, embodiments of the invention demonstrated a superior ability to deal with irregular fluctuations in the ambient light background, and particularly in the case of ambient light sources with narrow and intense spectral contributions. Library-based spectral matching demonstrated that beside a higher quality of reconstructed spectra, embodiments of the invention also benefit from a greater reproducibility of individual spectral reconstructions.

A measurement time advantage (up to 60% faster than "conventional" readout in experiments discussed below) and a data volume advantage (up to 18-times smaller file sizes in the experiments) are further benefits of the described techniques. In these experiments, PTFE was used as a test sample and Raman spectra were recorded at 830 nm excitation with additional fluorescent or incandescent light illumination. Results demonstrated that modes of operation embodying the invention (and operated in these experiments with first and second intervals switching over at 1000 Hz) had a clear benefit over the "conventional" mode (limited in practice to single mode exposure periods of ≤10 Hz) for the removal of dynamically changing ambient light contributions from Raman spectra. Library-based spectral matching revealed superior reconstruction performance and improved reproducibility for individual spectra using the "charge-shifting" mode, particularly for interfering lights with spectrally narrow lines and spatially inhomogeneous emission profiles.

The described apparatus and methods therefore overcome fundamental technical limitations of conventional CCD operation and are particularly advantageous for mobile Raman systems as applied under dynamically changing lighting conditions outside usual laboratory environments.

BRIEF DESCRIPTION OF THE DRAWINGS

Embodiments of the invention will now be described, by way of example only, with reference to the accompanying drawings, of which:

FIG. 2a demonstrates row shifting of background spectral signals B and Raman spectral signals R between groups of rows of CCD pixels in operation of the apparatus of FIG. 1;

FIG. 2b is similar to FIG. 2a but where first and second Raman spectral signals R1 and R2, which are accumulated using two different laser probe light wavelengths, are row shifted between groups off rows of CCD pixels;

FIG. 9a shows results for "static" conditions of minimal variation in ambient light, whereas FIG. 9b shows results for "dynamic" rather more variable conditions in ambient light. In these experiments, the ambient light was provided by a compact fluorescent tube.

DETAILED DESCRIPTION OF EMBODIMENTS

Figure 1:
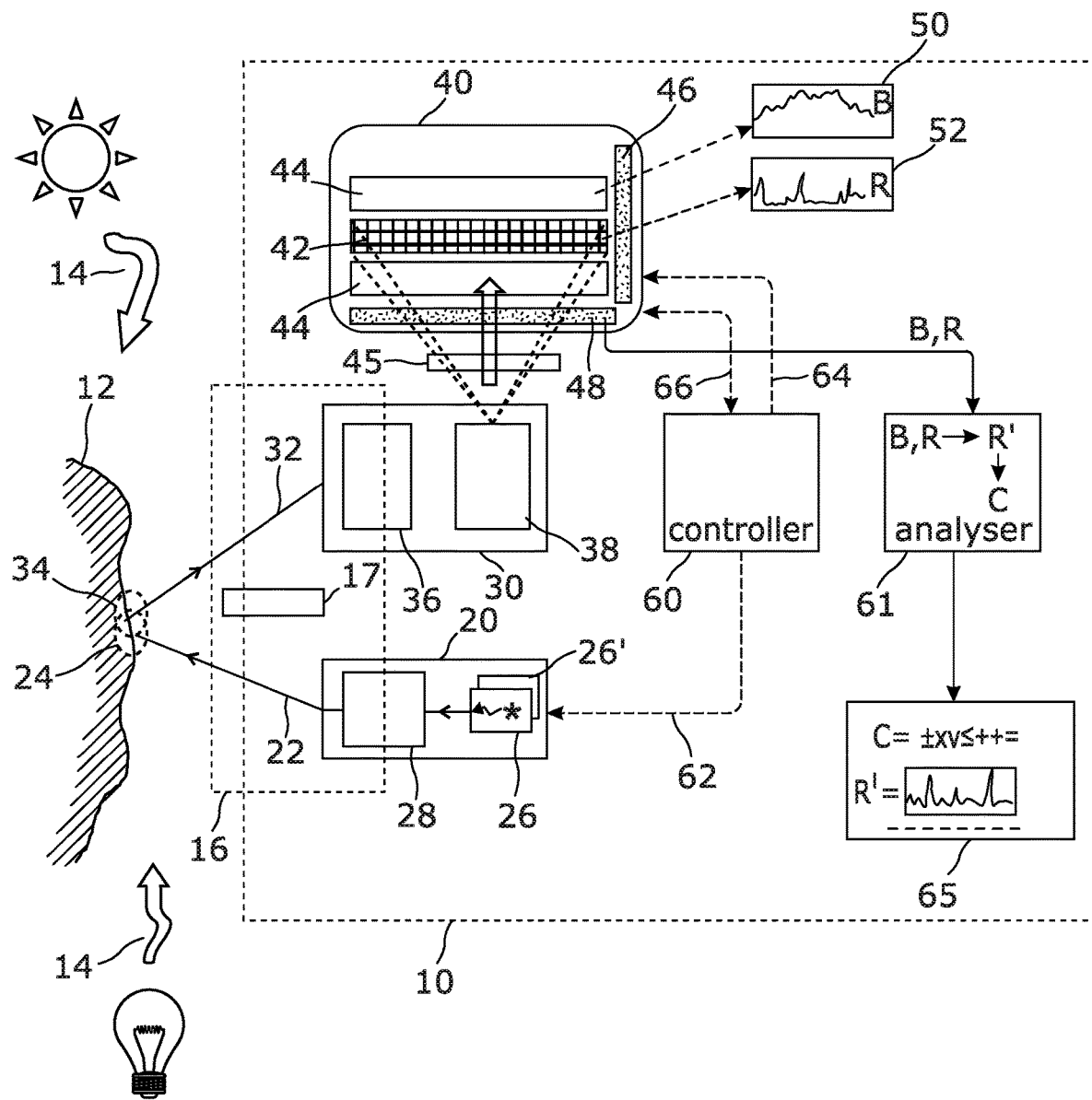
FIG. 1 schematically shows apparatus for detecting Raman spectral features of a sample under conditions of variable background light received from the sample such as variable ambient light, and/or fluorescence of the sample which diminishes over an exposure period due to photobleaching.

Referring now to FIG. 1 there is illustrated schematically apparatus 10 for detecting Raman spectral features of a sample 12 under conditions of variable background light from the sample. The embodiments are largely described with respect to the challenge of compensating for variable ambient light 14, but embodiments are also applicable to situations where background light received from the sample includes different or additional variable components such as fluorescence of the sample. Such fluorescence may for example diminish due to photobleaching of the sample over an exposure period.

Therefore where ambient light scattered from or received from the sample is referred to, this may more generally be taken as background light received from the sample in addition to elastically and inelastically scattered components of the laser light, of which the Raman scattered components are of particular interest for determining Raman spectral features and therefore characteristics of the sample.

Ambient light arriving at the sample may arise from various natural sources such as the sun, and/or various artificial sources such as incandescent, fluorescent, and LED lighting, and may be variable for example due to movement of people and objects around the apparatus, movement of the apparatus and/or sample, cloud movements across the sky, lights being turned on and off or otherwise varying in intensity and spectral output, and so forth. Variable levels of fluorescence may be emitted by the sample even if no ambient light arrives at the sample.

Acquiring sufficient Raman scattered light from the sample 12 to determine one or more chemical characteristics of the sample, while avoiding excessive laser light illumination intensities which could damage the sample, may typically require exposure periods of at least 0.1 seconds, and more typically a few to a few tens of seconds, and in any case longer exposure times will generally lead to greater accuracy of determination of such characteristics. In situations where it is not easy or convenient to exclude all ambient light 14 from the sample, significant variations of the ambient light in intensity and/or spectral content over such exposure times may make accurate measurement of Raman spectral features in light scattered from the sample more difficult. Even if ambient light is excluded from the sample, significant variations in fluorescence of the sample over such exposure times may make accurate measurement of Raman spectral features in light scattered from the sample more difficult.

Such difficulties may particularly arise if the apparatus 10 as a whole is a handheld or portable or self-contained device, or a probe portion 16 of the apparatus 10 is handheld for example being functionally connected to the rest of the apparatus by optical fibre connections. Such apparatus may be particularly useful for example at airports, warehouses, in security or military situations such as when explosives, toxins or other hazardous materials are suspected, by security or customs or law enforcement officers or military personnel, and so forth.

The apparatus 10 comprises a laser light source 20 which generates and directs laser probe light 22 to one or more illumination points or regions 24 on a surface of the sample 12. Collection optics 30 then receives collected light 32 scattered from one or more collection regions 34 of the surface of the sample 12. This collected light 32 includes both elements of the laser probe light 22, including elastically scattered portions and Raman scattered portions of that light, and elements of the ambient light 14 in particular such elements which have been scattered from the sample.

The laser light source 20 may typically comprise one or more lasers 26, and source optics 28 which may be used to condition the output of the laser in various ways and to direct the conditioned output towards the sample 12. The laser or lasers 26 may typically be provided by a near infrared laser, emitting a beam of laser probe light in the near infrared region of the electromagnetic spectrum, for example at a wavelength of around 800 nm.

In some embodiments only a single laser wavelength is needed, and this can conveniently be provided by a single laser 26. In some other embodiments, more than one wavelength of laser light is required, and this can be provided for example by a single laser 26 with controllable wavelength output, or by multiple lasers 26, 26' arranged to output at different wavelengths.

The source optics 28 may include one or more suitable band pass filters and other components for conditioning the beam, and one or more optical fibres and/or lenses arranged to direct the laser probe light 22 so as to be incident at the illumination region(s) 24 on the sample surface. If the apparatus 10 comprises a handheld or similar probe portion 16 then such optical fibres may be used to carry the laser probe light 22 to the probe portion 16 for subsequent delivery on to the illumination region 24 of the sample.

In a first aspect, the laser light source 20 is controlled by a controller 60 such that the laser probe light 22 is incident on the sample and scattered to form part of the collected light 32 during second time intervals of operation, but not during first time intervals of operation, and these intervals are described in more detail below. This may typically be achieved by controlling the laser 26 to generate the laser probe light 22 during the second intervals but not during the first intervals, for example by changing an input current to the laser to be above and below a laser threshold current respectively. In FIG. 1 this is shown as controlled by laser modulation signal 62. However, other techniques may be used instead or as well, for example including shuttering the output of the laser 26 using mechanical or optical arrangements, redirecting the laser probe light 22 elsewhere such as to a different position on the sample where little or no collection takes place by the collection optics 30, and so forth.

In a second aspect, the laser light source 20 is controlled by a controller 60 such that laser probe light 22 is incident on the sample and scattered to form part of the collected light 32 during both first and second time intervals of operation, but with laser probe light of a different wavelength being directed to the sample in each of the first and second intervals.

The collection optics 30 are arranged to collect light 32 from one or more collection regions 34 on a surface of the sample and to direct the collected light to detection pixels 42 of a pixelated, imaging, light detector in the form of a charge coupled device (CCD) 40. This collected light which is directed to the detection pixels includes scattered laser probe light 22 during the second interval, but not during the first interval.

The collection optics 30 may typically comprise receiving optics 36 arranged to receive light from the collection region 34 of the sample, such as suitable optical fibres and/or lenses, and to carry out any required spectral filtering such as by using one or more edge filters to exclude light not in the Raman scattering wavelength range to be detected and measured. If the apparatus 10 comprises a handheld or similar probe portion 16 then optical fibres of the receiving optics 36 may be used to carry the collected light 32 from the probe portion 16 for subsequent delivery on to the detection pixels of the CCD 40.

The collected light 32 may be delivered to the detection pixels 42 of the CCD 40 through a spectrometer 38 which is arranged to disperse the collected light 30 across the detection pixels to form a spectrum comprising Raman spectral features such as Raman peaks and/or lines, or otherwise distribute spectral features of the collected light, across these pixels. The spectrometer 38 may comprise for example one or more spectrally dispersive gratings or refractive elements, for example a holographic transmission grating, or a more complex spectrometer component such as a Holospec device from Kaiser Optical Systems. In some embodiments, spectral filtering techniques may be used as well as or instead of a dispersing spectrometer 38 to enable spectral features to be distributed across the detection pixels.

In some arrangements and modes of operation, it may be desirable for the illumination region(s) 24 and collection region(s) 34 to be exactly coincident, or as close to coincident and fully overlapping as possible, so that the maximum amount of laser probe light 22 is scattered into the collected light 32. However, the apparatus 10 as a whole if provided as a handheld or portable device, or a hand held probe 16 of the apparatus, may typically be arranged for use by holding proximally to but spaced from the sample, which will tend to make this exact or close alignment challenging. To this end one or more alignment mechanisms 17 may be provided as part of the apparatus, device or probe to help in controlling the alignment of the illumination and collection regions on the sample surface, for example by way of a mechanical positioning element such as a cone or frame extending from the device or probe which is touched on or pressed to the sample, or an optical arrangement such as visible light spots which provide a suitable guide.

The illumination 24 and collection 34 regions may be approximately circular or elliptical in form, but other shapes may be used such as annuli, regions formed of multiple separated sub regions and so forth. In some arrangements, as discussed in more detail below, the illumination and collection regions may be deliberately spaced apart by a spatial offset in order to determine characteristics of one or more subsurface regions of the sample using a SORS technique. By repeating spectral measurements with each of multiple such offsets, Raman spectral signals from each such offset can be associated with a different depth or distribution of depth within the sample, for example as discussed in WO2006/061566.

It has already been mentioned above that in some aspects the controller 60 is used to control the laser light source 20 such that during each first interval, substantially only ambient light contributions are found in the collected light 32, while during each second interval, the collected light 32 also contains contributions from the laser probe light 22 scattered at the sample 12. The timings of the first and second intervals are also communicated to the CCD 40, for example by means of a corresponding external trigger signal 64 as shown in FIG. 1.

At least first and second separate sets of accumulating signals are retained in the pixels of the CCD. The first set of accumulating signals, which we will refer to as background spectral signals 50, is loaded into the detection pixels 42 for the start of each first interval, so that during the first interval the charge in those pixels accumulates due to incidence of collected light 32 containing ambient but no laser probe light contribution, and these background spectral signals 50 as represented by the pixel charge therefore accumulate during each first interval. The second set of accumulating signals, which we refer to as Raman spectral signals 52, is loaded into the detection pixels 42 for the start of each second interval, so that during each second interval the charge in those pixels increases due to incidence of collected light 32 containing both ambient and laser probe light contributions, and these Raman spectral signals 52 as represented by the accumulating charge therefore also accumulate.

When not loaded into the detection pixels, a set of spectral signals 50, 52 is stored in other pixels of the CCD, which we refer to generally as storage pixels 44. Detailed and various options for locations of these storage pixels within the array of CCD pixels are discussed below. Between each of the first and second intervals, transfer of the background and Raman spectral signals between the detection pixels and the storage pixels can be achieved using row shifting of the CCD pixels, whereby entire rows of pixels are moved up or down the CCD pixel array, as discussed in more detail below. This movement of pixel groups can be achieved by suitable programming and/or control of control circuitry 46 of the CCD in response to the controller 60 indicating the timing of the first and second intervals.

In other aspects, laser light of a first wavelength as well as ambient light is incident on the sample during the first intervals, and laser light of a second wavelength as well as ambient light is incident on the sample during the second intervals, in which case the two sets of accumulating and stored spectral signals may be referred to as respective first and second Raman signals instead of background and Raman signals. A similar technique may be used even if ambient light is excluded from the sample, in order to compensate for other background light received from the sample, and in particular for fluorescence which is likely to vary over the duration of the measurement or exposure period, for example due to photobleaching.

The storage pixels 44 may conveniently be provided in two blocks each of the same pixel array size, respectively above and below the rows of the detection pixels which are also provided as a block of pixels of the same pixel array size as each storage block, as illustrated in FIG. 1, but other arrangements may be used as discussed further below for example in discussion of FIGS. 2a to 6.

In some arrangements, masking 45 may be needed to ensure that collected light 22 is not incident on the storage pixels. Such masking 45 could be provided by a mask component within the collection optics 30, or between the collection optics and the CCD 40. Alternatively or additionally the masking 45 could be implemented directly onto the CCD for example by adding one or more opaque layers (such as metallization) to the CCD over the storage pixels. In the arrangement of storage pixels shown in FIG. 1 this may not be necessary because the storage pixels are provided in contiguous pixel blocks separate to the block of detection pixels 42, but in other arrangements for example where detection pixel rows and storage pixel rows are interleaved singly or in smaller blocks then such masking 45 may be necessary.

At the end of an exposure period, readout circuitry 48 of the CCD is used to read out both the first spectral signals 50 (background or first Raman spectral signals) accumulated over the first intervals of the exposure period (denoted in FIG. 1 only as B, although the term R1 could be used for first Raman spectral signals), and the second spectral signals 52 (Raman or second Raman spectral signals) accumulated over the second intervals of the exposure period (denoted in FIG. 1 as R, although the term R2 could be used for second Raman spectral signals). This may be in response to a readout trigger signal 66 from the controller 60, or triggered internally within the CCD with the CCD instead sending a readout trigger signal 66 to the controller 60 to indicate the start of a readout operation.

The read out spectral signals are then passed to an analyser 61 which can use these signals in various ways. The various pixels of the CCD may then be reset and a further exposure period may begin with new background and Raman spectral signals (or first and second Raman spectral signals) being accumulated in the same way as before.

The analyser may be provided by one or more computer systems which may be general purpose computer systems or computer systems specifically arranged for the analysis purposes described herein. Such computer systems may typically comprise at least one microprocessor, suitable data input and output facilities, and memory storing computer program instructions for execution on the one or more computer systems for carrying out the described analysis aspects. To this end, data representing the various spectral signals may be passed to the analyser and stored in the memory for processing using the computer program instructions. Results of the analysis such as compensated spectral signals and/or chemical characteristics of the sample derived from the spectral signals, may be stored in the memory and/or output in various ways for example by display of a visual display of the analyser, by being passed to other computer systems for example over a data network, by being stored in a removable computer readable medium and so forth.

In particular, the analyser 61 may carry out various data analysis processes using the background and Raman spectral signals B, R, or first and second Raman spectral signals R1, R2, whether from a single exposure period, or from a combination of multiple exposure periods. In particular, compensated Raman spectral signals R' from which the contribution of ambient light has been largely removed, can be calculated from the background and Raman spectral signals, for example by a direct or scaled subtraction of the background signals from the Raman signals, or other techniques. Similarly, various techniques can be used for calculating compensated Raman spectral signals R' from first and second Raman spectral signals R1, R2.

Where first and second Raman spectral signals R1, R2 are accumulated and output, these will include corresponding spectral features arising from chemical properties of the sample, but shifted in wavelength from each other by the difference in wavelength between the first and second different wavelengths of the laser probe light. Wavelength differences between different laser probe light wavelengths of just a few tenths or even just a few hundredths of a nanometer may be sufficient for these purposes.

The analyser can then combine or compare the first and second Raman spectral signals R1 and R2 (and if available as discussed below also use further background spectral signals B), in order to determine compensated Raman spectral signals. Since the spectrum and intensity of fluorescence from the sample is essentially unaffected by the small differences in wavelength required between the first and second wavelengths of the laser probe light, this technique also has the advantage of permitting fluorescence to be largely removed from the compensated Raman spectral signals. This technique is also able to largely remove the spectral signal of any ambient light from the compensated Raman spectral signals, since any ambient light signals present in each of the first and second Raman signals is essentially the same, and the only systematic difference between the signals is therefore due to the different laser probe light wavelengths between the first and second intervals.

Note that, whether or not ambient light is received from the sample, combining first and second Raman spectral signals R1, R2 in this way also has the effect of helping to compensate for variations in fluorescence received from the sample over an exposure period. This technique can therefore be used to provide Raman spectral signals compensated for photobleaching and similar effects, including in apparatus and methods where ambient light is largely or completely excluded from the sample.

One or more characteristics of the sample, especially chemical characteristics C, can be derived from the compensated Raman spectral signals R', for example by establishing magnitudes of particular spectral peaks or lines expected in the Raman signatures of various chemical species. Such chemical characteristics could include for example identities and/or concentrations of chemical species in the sample.

By interleaving the detection of the Raman spectral signal and the background spectral signal multiple times over an exposure period of the CCD before the CCD is then read out, as described above, it is easier to optimize the length of each respective interval such that the background spectral signal can more accurately reflect the contribution of ambient light to the Raman spectral signal. Similarly, if first and second Raman spectral signals are accumulated in each of the first and second intervals respectively then the respective intervals can more accurately reflect the same contributions of ambient light (and/or sample fluorescence). In both cases, moreover, the number of readout operations from the CCD is also greatly reduced thereby also reducing the level of readout noise.

Data such as spectra, spectral feature intensities or magnitudes, and other aspects of the compensated Raman spectral signals R', and/or data describing particular chemical characteristics C of the sample for example providing the concentration or indicating the presence of a particular species, may be presented using a display 65 of the apparatus 10, or stored in the apparatus 10 for example in fixed or removable data storage media, or output to other data processing equipment such as other computers (not shown in FIG. 1) whether connected over a network or more directly connected to the apparatus 10.

Over an exposure period, there may be a large number of first and second intervals, for example, at least 10 of each, at least 100 of each, or at least 1000 of each, and for example with the first and second intervals alternating in a repeated cycle. Where the letters B and R represent the intervals during which the background and Raman spectral signals are accumulated, such a cycle could be written as [B, R]. However, it is not strictly necessary to have exactly the same number of each interval in a single exposure period (for example it may be common to have the number differ by one even if strictly alternating), and somewhat different numbers might be used if there are more first and second intervals as mentioned below. The same applies for other aspects where the intervals during which first and second Raman spectral signals R1, R2 are accumulated.

Typically, the first and second intervals may all be of the same duration, for example each lasting around 1 millisecond, although the first intervals may be of different length to the second intervals if required. For example, an external trigger signal 64 to the CCD with a frequency of about 1 kHz could be used. The duration of a row shift period during which either the background (or first Raman) spectral signals 50 or the Raman (or second Rama) spectral signals 52 are shifted in either direction between the detection pixels 42 and the storage pixels 44 will depend on various factors, but may be significant in comparison to the duration of a first or second interval. For example, if the CCD is capable of shifting data between adjacent pixel rows at a rate of 1 MHz and the detection pixels form a block of 80 rows, the row shift period between any two intervals will take around 0.08 milliseconds. If this time period is subtracted from a 1 millisecond period available between subsequent repeats of the external trigger input then only about 0.9 milliseconds is available for each of the first and second intervals.

In the arrangement of FIG. 1 no shuttering of the CCD is implemented in the row shift periods between the first and second intervals, so that collected light 32 will continue to be incident on the detection pixels during those times. To avoid the risk of laser probe light 22 being incident on detection pixels during the row shift periods and thereby contaminating the background spectral signals, it is preferable to ensure a sufficient time buffer at the start and end of the second interval during which no laser probe light 22 is directed to the sample, for example by turning off or shuttering the laser 24 for those buffer periods. Suitable buffer periods could be for example around 50 milliseconds at the start and end of each second interval. Bearing this in mind, it is clear that in many cases no laser probe light will be incident on the detection pixels for at least a part of each second interval, for example during such buffer periods.

If a mechanical, optical or electronic shuttering mechanism is used to prevent collected light 32 from arriving at the detector pixels except during the second intervals then such buffer periods might be largely avoided. Such shuttering could also be used to prevent collected light from arriving at the detector periods during row shift periods if required.

Although as described above the apparatus of FIG. 1 can be used to accumulate background spectral signals 50 representing the background such as the ambient light 14, and Raman spectral signals 52 representing both the laser probe light 22 and background/ambient light 14, as received in the collected light 32, or alternatively first and second Raman spectral signals as discussed above, one or more further spectral signals may also be accumulated over one or more further intervals in the repeated cycle. In such cases, two or more such spectral signals will usually be retained in the storage pixels while one of the spectral signals is held in the detection pixels.

An example of such an arrangement is when the exposure period comprises repeated third intervals, and during each third interval laser probe light 22 is scattered into the collected light 32 by a reference sample instead of by the sample 12. This could be implemented by incorporating a reference sample into the apparatus 10 and adapting the laser light source 20 and/or collection optics 30 appropriately, or by swapping the sample and reference sample repeatedly into and out of the probe light for example using a movable or rotating stage. Resulting accumulated reference spectral signals F can then be output at the end of an exposure period by the CCD for use by the analyser 61 in determining difference spectral signals by a comparison of Raman spectral signals 52 and the reference spectral signals, with the Raman spectral signals and/or the difference spectral signals being compensated for the effects of background or ambient light using the background spectral signals. In this way Raman difference spectral signals representing differences between the spectral signals from the sample and the reference sample can be determined, and can also be provided with compensation for background or ambient light as discussed above.

In other arrangements, where first and second Raman spectral signals are collected in first and second intervals, a third interval may involve collecting only background or ambient light scattered from the sample, with no laser probe light being incident on the sample in that third period, in a manner similar to the collection of a background spectral signal discussed above.

If three or more different intervals are used in this way to measure three or more different spectral signals at the CCD for output at the end of the exposure period, then various options exist for a repeated cycle of the three or more different intervals. If the intervals are each represented by the letters B, R, F corresponding to the background, Raman and reference spectral signals accumulated during those intervals, then cycles could include repeated [B,R,F,R], [B,R,F,B,R,F] and various other permutations, noting that it is not necessarily a requirement to have the same number of each interval in the cycle, and that the lengths of the intervals may be different and moreover vary from cycle to cycle.

If the first, second and third intervals in this case are represented by the letters B, R1, R2 corresponding to the background, first Raman and second Raman spectral signals accumulated during these intervals, then cycles could include repeated [B, R1, R2], [B, R1, B, R2], and various other permutations, noting that it is not necessarily a requirement to have the same number of each interval in the cycle, and that the lengths of the intervals may be different and moreover vary from cycle to cycle.

In the above examples, third and optionally further different laser probe light wavelengths may be used for the purposes of obtaining third R3 and optionally further (R4 etc.) Raman spectral signals, with each of the Raman spectral signals being combined together, optionally with one or more background spectral signals, in the calculation of compensated Raman spectral signals. In such cases, the cycles could include repeated intervals such as [R1, R2, R3], [B, R1, R2, R3], [B, R1, B, R2, B, R3], [R1, R2, R3, R4] or various other permutations, with each of the spectral signals being accumulated in the detection pixels for the corresponding interval, and being stored in the storage pixels at other times.

A single laser 26 may be operated to provide laser probe light at the required two or more different wavelengths, or multiple lasers 26 could be included in the probe light source 20 for this purpose.

Various mathematical and analytical techniques may be used for combining first, second and optionally further Raman spectral signals optionally with background spectral signals to determine compensated Raman spectral signals, for example as discussed in U.S. Pat. No. 8,570,507, the contents of which are incorporated herein by reference for this particular and all other purposes. For example, one option is to perform a scaled subtraction of the first and second Raman spectral signals, and in many cases this procedure will be acceptable because the resulting derivative-like compensated Raman spectral signals are of sufficient quality and can be subject to further data analysis. Under some circumstances it may be necessary to calculate reconstructed spectra from the derivative-like compensated Raman spectral signals to improve the spectral quality, for example in terms of signal-to-noise-ratio. This can be achieved by a simple integration procedure of the difference Raman spectral signals for example as discussed in Matousek et al., *Appl. Spectrosc.* 2005, 59, 848-851, the contents of which are incorporated herein by reference for this particular and all other purposes.

Depending on the specific application, more advanced algorithms for reconstruction of the compensated Raman spectral signals may be required as well. As an example, WO2011/033017 (the contents of which are incorporated by reference herein for this particular and all other purposes) describes such a procedure where first Raman spectral signals and second Raman spectral signals are standardized in relation to one another in terms of intensity values. First difference spectral signals are subsequently calculated, second difference spectral signals are calculated, the first difference spectral signals are converted into first transformation spectral signals, the second difference spectral signals are converted into second transformation spectral signals, and finally the compensated Raman spectral signals are calculated by adding the first transformation spectral signals and the second transformation spectral signals.

Suitable CCD devices 40 with sufficient sensitivity may typically be cooled to low temperatures, for example using Peltier elements or liquid nitrogen, to reduce noise, and may typically have pixel arrays with dimensions of a few hundred to a few thousand pixels in the row and column directions. The detector pixels 46 then may typically comprise a few tens of rows of pixels, for example 80 rows, and typically of full row length (for example 1000 pixels) although shorter rows of pixels could be used. The collection optics is then used to spectrally disperse the collected light 32 in a direction along the rows of detection pixels as discussed above. In order to store spectral signals when not in the detector pixels, at least one corresponding subset of the storage pixels is typically required for each such spectral signal, with each subset typically corresponding in dimensions and geometry to the detection pixels. Therefore, if the detection pixels are provided by full length rows of 80 pixels, the storage pixels should provide two corresponding regions of full length rows of 80 pixels.

Where each spectral signal is stored in multiple rows of CCD pixels, these rows may be averaged or summed together on the CCD itself before transfer to the analyser 61. This would typically be done before digitisation of the pixel charges. Similar combining of adjacent pixels along rows may also be carried out if desired to effectively reduce the spectral resolution but improve noise characteristics by the averaging. Alternatively, such summing, averaging or other combining of pixels, especially the combining of multiple rows, could be carried out at the analyser.

In FIG. 1 the geometry of the detection and storage pixels is depicted as provided by first and second blocks, each of multiple contiguous rows of storage pixels 44, lying above and below a block of contiguous rows of detection pixels. FIG. 2a illustrates how background spectral signals and the Raman spectral signals can be moved between these three equally sized pixel blocks, as cycles of first and second intervals are repeated during an exposure period.

The same principles and detail apply where instead of background and Raman spectral signals, first and second Raman spectral signals are accumulated as discussed above during intervals where the laser probe light has correspondingly two different wavelengths (Raman spectral signals R1, R2 instead of background and Raman spectral signals B, R). This is illustrated in the corresponding panels (i) to (iv) of FIG. 2b, where the "ambient" and "ambient+probe" light incident on the detection pixels 42 in FIG. 2a are replaced by "ambient+probe λ1" and "ambient+probe λ2".

In panel (i) of FIG. 2a, a central block of detection pixels 42 (shown in solid outline) is depicted with a first block 44' and a second block 44" of storage pixels (shown in heavy broken outline) being located above and below the central block on the CCD pixel grid. Each block could be, for example, around 80 adjacent pixel rows in height and around 1000 adjacent pixels in length. A guard region 47 of one or more rows not used as either detection pixels or storage pixels may be provided between each block, for example to better guard against collected light 32 being incident on the storage pixels.

In panel (i), accumulating background spectral signals B are held in the detection pixels 42, such that the background spectral signal accumulates under illumination from spectrally dispersed ambient light scattered from the sample in the collected light 32, but without any contribution from scattered laser probe light. The Raman spectral signals R are held in the lower block of storage pixels 44" which is not illuminated from the collected light 32. FIG. 2a therefore corresponds to a first interval as discussed above.

Panel (ii) of FIG. 2a depicts a subsequent row shift period during which the Raman spectral signals are being row shifted up into the detection pixels 42, and the background spectral signals are being shifted up into the upper block of storage pixels 44'. At the end of this row shift period a second interval begins as depicted in panel (iii), such that the Raman spectral signals accumulate in the detection pixels 42 under illumination of spectrally dispersed collected light 32 which, for at least part of the second interval, includes laser probe light 22 scattered from the sample as well as background or ambient light.

In panel (iv) it can be seen that after the end of the second interval the Raman spectral signals are shifted back down to the lower block of storage pixels 44", and the background spectral signals are shifted down to the detection pixels 42, so that a next cycle of first and second intervals can begin.

Although in panels (i) to (iv) of FIG. 2a the spectral signals are depicted as slightly smaller blocks than the pixel blocks in which they are stored at various times, this is only for clarity purposes so that the various components can be more clearly seen in the figures.

Figure 3:
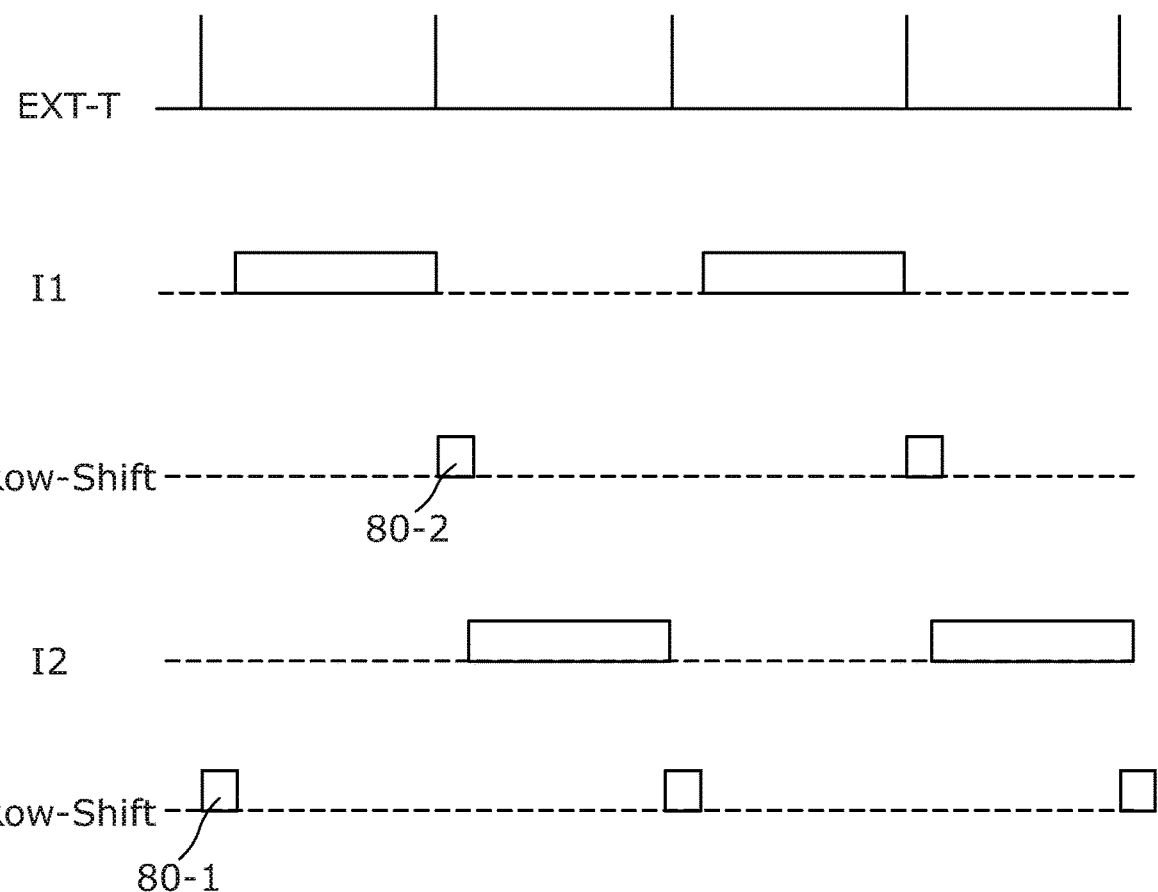
FIG. 3 provides a timing diagram of the operations illustrated in FIG. 2a or 2b.

FIG. 3 is a timing diagram showing how the events of FIG. 2a or 2b develop over time from left to right in the figure. Although the discussion below will focus on the timing of FIG. 2a, it can easily be seen how this translates to timing of the FIG. 2b process. A signal indicating or controlling timing of the cycle of intervals is indicated at the top of the diagram, as EXT-T, which for example could be the external trigger signal 64 discussed above in connection with FIG. 1. At the left of the figure, a peak in this trigger signal causes or indicates the start of a first row shift period 80-1 such as that depicted in panel (iv) of FIG. 2a where the background spectral signals are row shifted into the detector pixels, following which an instance of the first interval I1 begins. The end of this first interval is triggered or indicated by a second peak in the EXT-T signal which causes or indicates the start of a second row shift period 80-2 in which the Raman spectral signals are row shifted into the detector pixels and an instance of the second interval I2 begins. This cycle is repeated a number of times during an exposure period, following which each of the background spectral signals and Raman spectral signals which have accumulated during the first and second intervals respectively, are read from the CCD.

Because, absent some further shutter mechanism, the detection pixels 42 are still illuminated by background or ambient light during row shifting periods, and because it may be difficult to project the dispersed collected light 32 onto the detection pixels entirely evenly (for example without some "smile" pattern or other distortion), the accumulated spectral signals may be affected to some minor extent by artefacts resulting from which of the spectral signals is stored above, and which below the detection pixel block. To reduce the impact of this asymmetry on output of the apparatus therefore, each exposure period consisting of cycles such as those shown in FIG. 2a or 2b where one set of signals such as the background spectral signals are stored above the detection pixels may be balanced by an exposure period consisting of similar cycles but where the same set of signals such as the background spectral signals are stored below the detection pixels.

Figure 4:
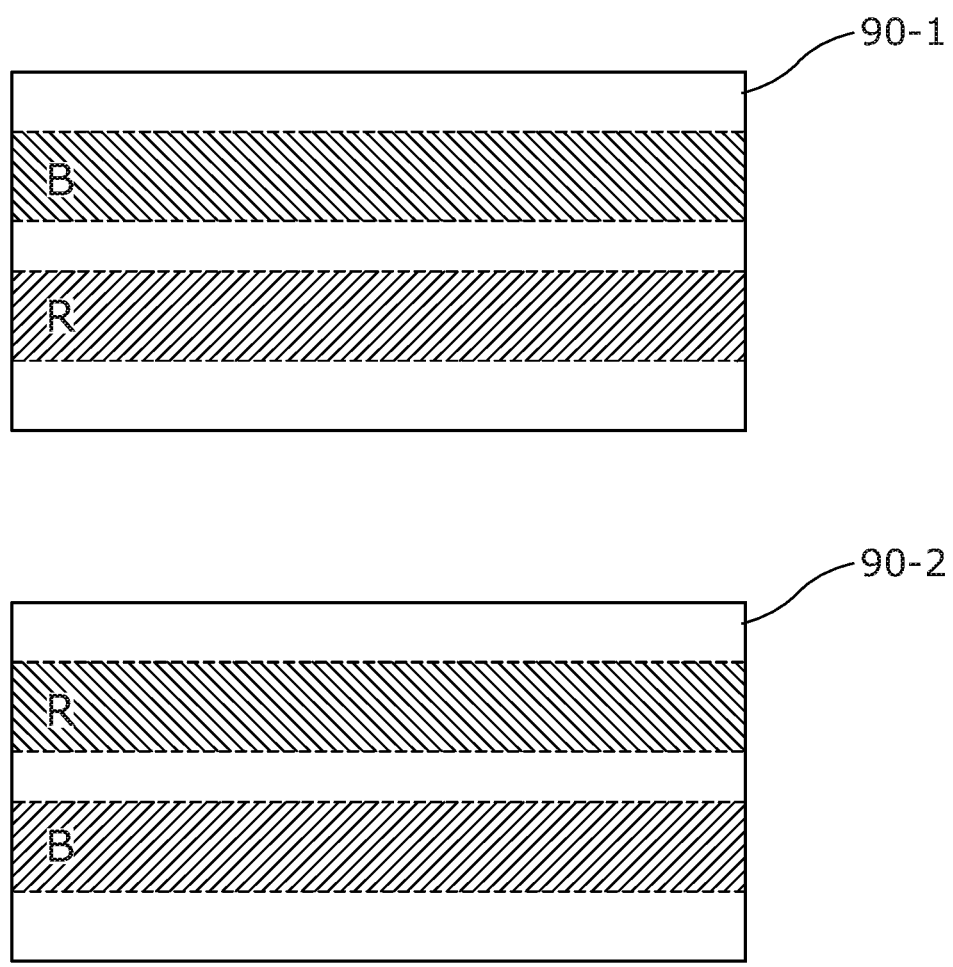
FIG. 4 shows a pair of CCD images containing background and Raman spectral signals in a symmetric pair.

Accordingly, FIG. 4 illustrates data read from the CCD at the end of two different exposure periods. The upper panel shows a read out "image" 90-1 formed of pixels in which the upper block B contains the accumulated background spectral signals, and the lower block R contains the accumulated Raman spectral signals, whereas the lower panel shows a read out "image" 90-2 formed of pixels in which the upper block R contains the accumulated Raman spectral signals, and the lower block B contains the accumulated background spectral signals.

It may be advantageous to interleave the alternate exposure periods corresponding to 90-1 and 90-2 in FIG. 4, so that adjacent such sets of data can be paired and combined to better reduce the above artefacts, but in any case more generally, an equal or similar number of exposure periods using the alternate positions for storage of the background and Raman signals should be combined or used in further analysis of the data, for example in compensation of the Raman spectral signals using the background spectral signals.

The techniques shown in FIG. 4 and discussed above equally apply where first and second Raman spectral signals R1, R2 are accumulated using laser probe light of two different wavelengths, as discussed above, instead of the background and Raman spectral signals B and R as shown in the figure.

Figure 5A:
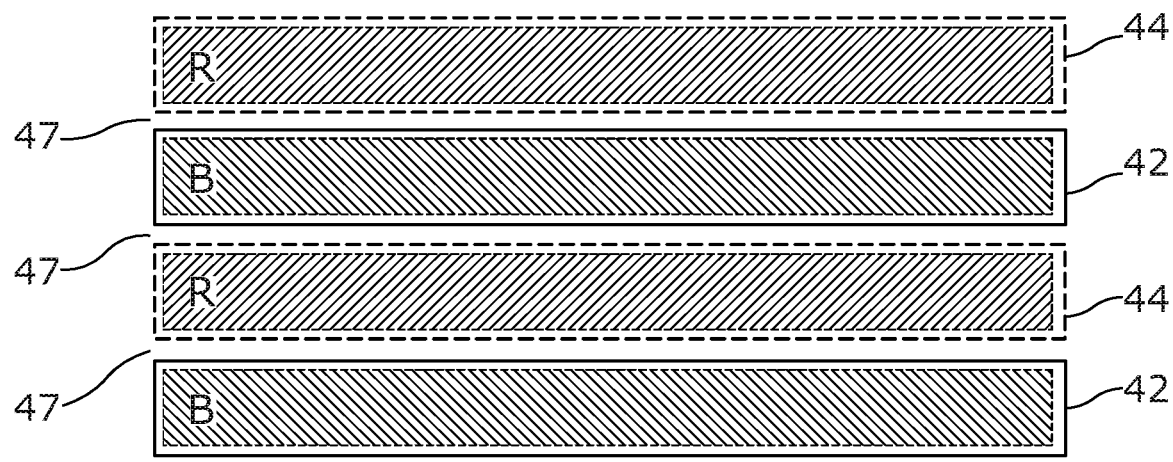
FIG. 5 shows how background spectral signals B and Raman spectral signals R (or similarly R1 and R2, referring to FIG. 2a above) can be interleaved and shifted in the CCD pixels.
Figure 5B:
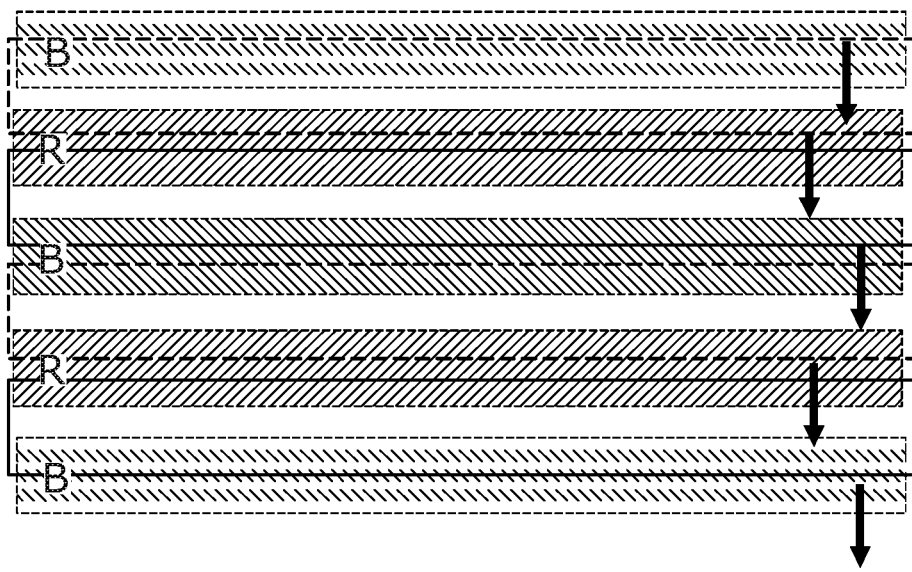

FIGS. 5a and 5b show an alternative scheme for arranging the detection pixels and storage pixels. In this arrangement there are multiple blocks of detection pixels 42, interleaved with corresponding blocks of storage pixels, each block having fewer rows than in the examples of FIGS. 2 and 4. Each block could be as small as one pixel row in height, or could be larger ranging to several tens of pixels or more in height. Typically, each block of storage pixels is of the same size in terms of pixels as each detection block. FIG. 5a then represents a first interval during which each block of detection pixels 42 contains background spectral signals B for accumulation under illumination of the spectrally dispersed collected light 32, and each storage block 44 contains Raman spectral signals R which are not illuminated.

FIG. 5b represents a row shift period at the end of the first interval during which the background spectral signals B in each block of detection pixels are row shifted down to the storage blocks 44 beneath, and the Raman spectral signals R in each block of storage pixels are row shifted down to the detection blocks 42 beneath. A second interval then takes place for accumulation of the Raman spectral signals, following which a further shift in the reverse direction to that of FIG. 5b, or optionally in the same direction, takes place, to return to the start of a subsequent first interval as depicted in FIG. 5a. The shifting sequence between successive intervals could follow a binary -up-down-up-down- scheme, or alternatively a different scheme involving successive shifts in the same direction such as -up-up-down-down- although this is liable to use more blocks of pixels for storage and detection.

The arrangement shown in FIGS. 5a and 5b also applies where first and second Raman signals R1 and R2 are accumulated in the detection pixels using laser probe light of two different wavelengths, instead of the background and Raman spectral signals as shown.

In arrangements where the blocks of detection pixels and blocks of storage pixels are interleaved, more sophisticated or finer masking 45 (see FIG. 1) may be required to ensure that the storage pixels are protected from illumination by the collected light. The number of pixels in guard regions 47 may also be adapted for similar purpose. As discussed above, such masking 45 could be implemented by masking layers implemented directly on or in the CCD device, or elsewhere in the apparatus.

If each interleaved block of detection or storage pixels is only one row of pixels in height then this minimises the distance and therefore the time required to complete a row shift period between subsequent intervals. However, implementing blocks of just one or a few rows may make it more difficult to implement suitable masking of the storage pixels, so that blocks of several pixels in height, for example ten pixels in height may be more convenient. On the other hand, if just a single block of detection pixels is used as illustrated in FIGS. 1, 2a and 2b then this has the advantage that the collected light can be concentrated particularly to that block and more efficiently used than if spread over interleaved detector and storage pixel blocks.

Figure 6:
FIG. 6 demonstrates the implementation of a third set of spectral signals F interleaved on the CCD.

It was mentioned above that more than two sets of spectral signals (background and Raman spectral signals, or first and second Raman signals from laser probe light of different wavelengths) could be accumulated by the apparatus using one or more further intervals. One example discussed above is that in each third interval of a cycle, laser probe light 22 is scattered into the collected light 32 by a reference sample instead of by the sample 12. Resulting accumulated reference spectral signals F can then be output at the end of an exposure period by the CCD. FIG. 6 shows one way in which such third or further intervals and corresponding spectral signals may be implemented. Instead of interleaved single blocks of detector pixels and storage pixels as shown in FIG. 5, FIG. 6 shows two blocks of storage pixels interleaved between each pair of blocks of detector pixels.

By suitable sequences of row shifting of these blocks, each of the three sets of spectral signals B, F, R can be accumulated when present in the detection pixels 42 during a corresponding interval of each cycle, while being retained in the storage blocks 44', 44" during the other intervals. For example a suitable shift sequence here could be "-down-down-up+up-down-down-up+up-", where "up+up" indicates that spectral signals are shifted by twice the usual distance, that is by a distance of two blocks, in that row shifting period.

More than two sets of spectral signals can also be implemented using a single block of detector pixels along the lines illustrated in FIGS. 1 and 2a-2d, by adding one or more further blocks of storage pixels above and/or below the block of detector pixels.

The arrangements of FIG. 6 also apply where other combinations of three (or more) different signals are to be accumulated, for example a background spectral signal along with first and second Raman spectral signals accumulated using laser probe light of two different wavelengths B, R1, R2. Another example is where no background spectral signal, but first, second and third Raman spectral signals R1, R2, R3 are accumulated using laser probe light of three different wavelengths.

It was mentioned above that the illumination 24 and collection 34 regions as illustrated in FIG. 1 may be deliberately spaced apart by a spatial offset in order to determine characteristics of one or more subsurface regions of the sample using a SORS technique. By using multiple exposure periods each with a different such offsets, Raman spectral signals from each such offset can be associated with a different depth or distribution of depth within the sample, for example as discussed in WO2006/061566. Such techniques are particularly of relevance when the sample 12 is diffusely scattering and the laser probe light 22 can penetrate the surface of the sample to diffusely scattered over significant distances for example of at least a few millimetres.

The proportion of scattering of the laser probe light 22 within a diffusely scattering sample 12 which is inelastic Raman scattering, compared with the proportion of scattering which is elastic scattering is typically very small, usually with a difference of many orders of magnitude. As a consequence, most photons of probe light are not Raman scattered in a diffusely scattering sample. However, each photon of probe light which is Raman scattered within the sample is also subsequently scattered elastically a large number of times, giving rise to a random walk of the photon through the sample. The average path of this random walk through the subsurface volume of the sample, between the illumination region 24 and the collection region 34, depends on the spatial offset between these regions. It can be seen that for larger spatial offsets the average depth of the path will be deeper within the sample.

Using this principle, the spacing between the illumination and collection regions can be controlled or adjusted by the apparatus 10 in order to control the distribution of depths at which the Raman scattering occurs. This technique is referred to as spatially offset Raman spectroscopy (SORS), and is discussed in detail in WO2006/061565 and WO2006/

061566, the contents of which are incorporated herein by reference for all purposes, including for illustrating how characteristics of the sample may be determined at particular depths and profiles of depth within the sample.

Some ways in which Raman spectral features or related information from different spatial offsets may be combined to derive characteristics of the sample selected for one or more depths or one or more profiles of depths, are discussed in the above patent publications, but may include simple subtraction schemes for example in which the spectral features for a small or null offset are subtracted from those of one or more larger offsets, or more complex multivariate analysis, such as principal component analysis in which statistical relationships between detected spectral features at multiple offsets are used to derive sample characteristics at a depth, profile of depth, or multiple such depths or profiles of depth.

According to the principles of spatially offset Raman spectroscopy, therefore, the illumination and collection regions may be of various sizes and shapes, and for any particular spatial offset these regions may each be formed by single contiguous or multiple discrete segments on the surface of the sample. Some examples of such regions are depicted in FIGS. 7a and 7b.

Figure 7A:
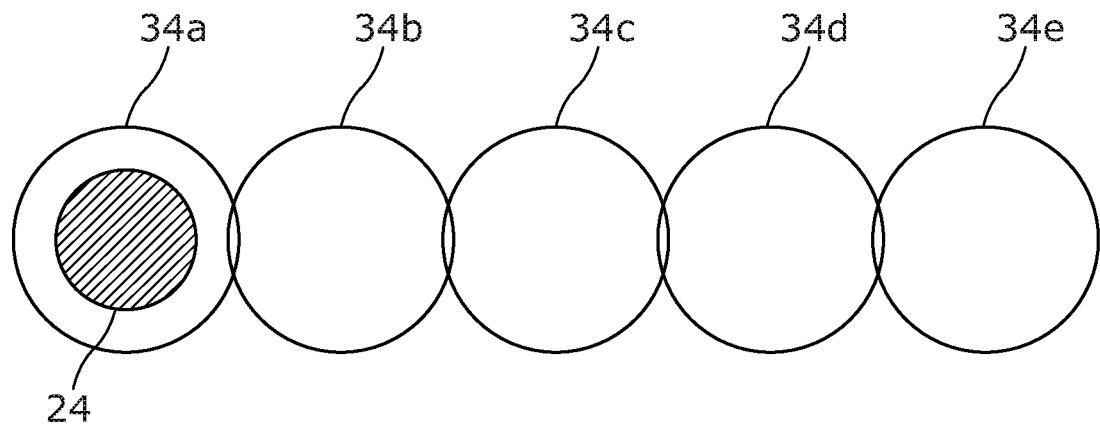
FIGS. 7a and 7b illustrate how aspects of the invention can be implemented to provide spatially offset Raman spectroscopy.

In FIG. 7a, an illumination region 24 is provided at a fixed position, and multiple collection regions 34a-34e are provided at increasing spatial offsets from the single illumination region. Optionally, one of the illustrated collection regions 34a is coincident with, or overlapping with the illumination region 24, so as to form a zero offset or null spacing. This zero offset can conveniently provide a signal representative of the surface of the sample, for compensating signals derived from larger signals. This can be done, for example, by subtracting Raman features detected for the null spacing from Raman features detected for one or more larger spacings.

Using the arrangement of FIG. 7a as an illustration, it will be seen that any number of spatial offsets between the illumination and collection regions may be used, for example from one up to ten or more offsets, with Raman features typically being detected during separate exposure time intervals for each offset. Although in FIG. 7a the illumination region remains fixed relative to the sample and the collection region is moved, the illumination region could be moved instead or as well as the collection region. The regions in FIG. 7a are essentially circular or elliptical in shape, typically determined by convenience of implementation of the delivery and collection optics, various other shapes may be used. In FIG. 7a none of the collection regions 34b-34e overlaps with the illumination region, but some overlap maybe permitted.

Figure 7B:
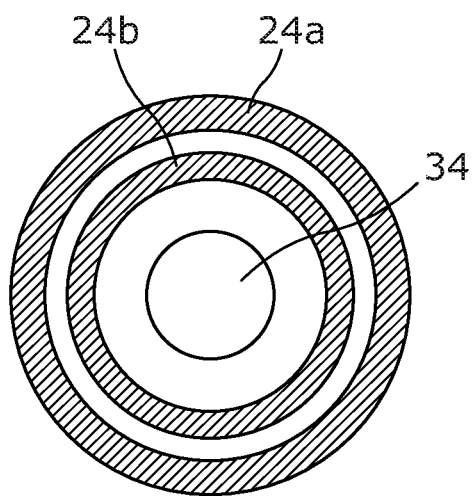

In FIG. 7b, a concentric arrangement is used in which a central collection region 34 lies within a surrounding illumination region 24a, which could be in the form of a continuous or broken annulus. This has an advantage in that the illumination region is relatively large, and therefore can be provided using a lower intensity of illumination to avoid damaging the sample. Multiple spatial offsets can then be provided by varying the radius of the illumination region, as depicted by concentric illumination regions 24a and 24b.

In order to provide sufficient scattering of the probe light to be able to detect Raman spectral features originating at depth with the sample, the sample may be diffusely scattering or turbid or strongly diffusing. The degree of such scattering will depend on the sample, and may be defined in terms of transport length which is a length over which the direction of propagation of photon of probe light is randomized. The skilled person knows that transport length l* of diffusive scattering may be taken as being related to the mean free path by the expression:

$$l^* = l/(1-g)$$

where g is the asymmetry coefficient (average of the scattering angle over a large number of scattering events), and l is the mean free path. The diffuse scattering transport length for some samples suitable for use with the present invention may be of the order of about 100 μm to a few mm.

To this end, the apparatus and methods describe above in respect of FIGS. 1 to 6 may therefore be used with one or more spatial offsets between the illumination and collection regions. Such offsets may typically range from about 1 mm to about 50 mm, and more typically from about 3 mm to about 20 mm, and for determining characteristics of the sample at depths within the sample of in the range from about 1 mm to about 30 mm and more typically from about 2 mm to about 15 mm. Embodiments of the invention may be arranged to determine such characteristics at just one depth or depth profile, for example using a single spatial offset between the illumination and collection regions, or may be arranged to determine such characteristics at each of multiple depths or depth profiles. Embodiments may also use a zero or null offset in order to determine a characteristic at the surface of the sample FIGS. 1, 7a and 7b depict illumination and collection regions which are adjacent, proximal, or spaced apart on a surface which is largely planar or only moderately curved. Such an arrangement may be described as a backscatter configuration, because after penetrating into the sample and undergoing Raman scattering in a sub-surface region, a photon of laser probe light is backscattered to the surface of the sample for collection by the collection optics. However, the illumination and collection regions may also lie on parts of the surface which are far from coplanar, with substantially different surface normals, for example with normals in the region of 90 degrees apart, or even in the region of 180 degrees apart, or any other angle or range of angles.

For example, the illumination and collection regions may be disposed on opposite sides of a sample, or such that a subsurface volume the characteristics of which are being determined by the invention lies directly between the illumination and collection regions, and such arrangements may be described as transmission configurations. Transmission arrangements in which material of the sample lies directly between the illumination and collection regions may be of particular interest where the sample is small, for example being only of the order of about 5 mm to about 50 mm in diameter or thickness for strongly scattering samples, although larger diameters or spacings between illumination and collection regions could be used for more transparent samples.

Further discussion of transmission geometries and other details of such arrangements which can be used in embodiments of the present invention, to determine pH of a sub-surface region of a sample, can be found in the prior art including WO2007/113566, the contents of which is incorporated herein by reference in its entirety, to demonstrate how to arrange suitable transmission geometries for use in the present invention, and for all other purposes.

Figure 8:
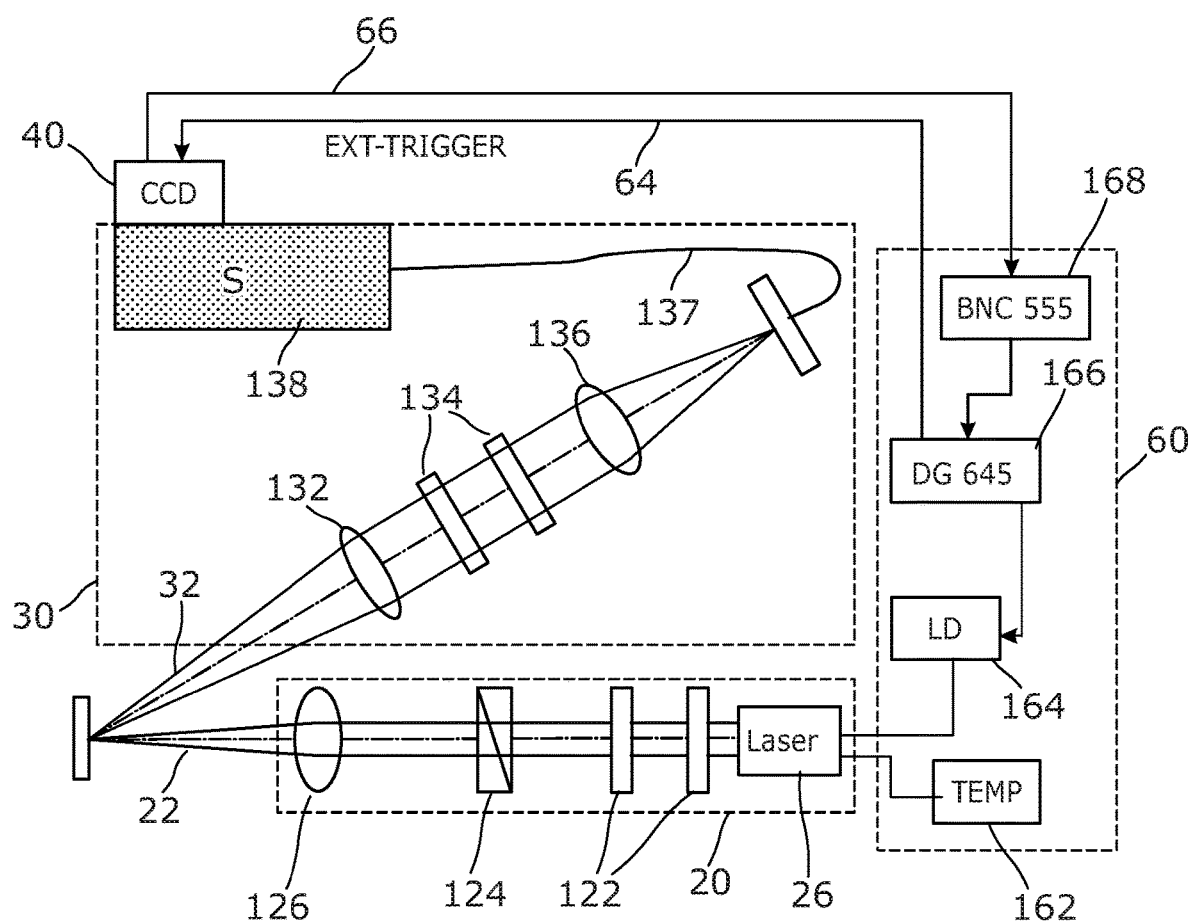
FIG. 8 shows in more detail how the arrangement of FIG. 1 may be implemented.

FIG. 8 depicts some ways of how the apparatus and methods discussed above may be implemented in more detail, although for clarity no details of spectral signal output from the CCD or subsequent analysis are shown in this figure. This figure shows how background and Raman spectral signals may be accumulated during first and second intervals of an exposure period, but could easily be adapted such that first and second Raman spectral signals are instead accumulated during the first and second intervals respectively, with laser probe light of first and second different wavelengths being incident on the sample in the first and second intervals respectively.

In the laser light source 20, the laser 26 is provided by a microsystem diode laser module (Ferdinand-Braun-Institut, Leibniz-Institut für Höchstfrequenztechnik, Berlin, Germany) emitting a collimated beam at 830 nm. In the source optics, the linearly polarized laser light passes through two bandpass filters 122 (Semrock, Inc.) and is then converted into circularly polarized light by means of a quarter waveplate 124. Although circularly polarized light was used in the experiments described below, this had no particular impact on the detection mode and equally good results would have been obtained with linearly polarized light or with any other stable state of polarization. The temperature of the laser module is adjusted to 25° C. by a temperature controller 162 (5240 TECSource, Arroyo Instruments) of the controller 60, and the injection current is controlled by a laser driver 164 (4220-DR LaserSource, Arroyo Instruments) also forming part of controller 60.

In the source optics, a lens 126 with a focal length of 50 mm then focusses the laser radiation onto a sample 12. In experiments described below, the sample was provided by a 220 μm thick layer of PTFE.

The laser radiation backscattered from the sample 12 is collected in the collection optics 30 by an achromatic lens 132 with a focal length of 100 mm. Subsequently, two Raman edge filters 134 (Semrock, Inc.) are transmitting only the Raman Stokes shifted components while rejecting the elastically scattered and anti-Stokes contributions. An achromatic lens 136 with a focal length of 60 mm focusses the light into a round-to-linear fibre bundle 137 (BFL200LS02, Thorlabs, Inc.) which then transfers the detected light into the spectrometer 138 (Holospec 1.8i, Kaiser Optical Systems, Inc.) with attached charge-shifting CCD 40 (DU420A-BR-DD-9UW, Andor Technology) thermo-electrically cooled down to −70° C. and controlled by a PC running Andor "Solis" software (version 4.28.30052.0, Andor Technology). The CCD was a standard spectroscopic CCD with no hardware modifications. The row shifting mode operations in the CCD as described above were facilitated by customization of the "Solis" software.

Both the laser source optics 20 and collection optics 30 were shielded from ambient light using a black aluminium foil cover (BKF12, Thorlabs, Inc.).

To synchronize the emission of laser probe light 22 with the interval cycles of an exposure period and subsequent data read out, one of the output ports of a first digital delay generator 166 (DG645, Stanford Research Systems) is connected to the external trigger input 64 of the CCD while another is connected to the modulation input of the laser driver 164. The shutter output 66 of the CCD is connected to the input of a second digital delay generator 168 (Model 555, Berkeley Nucleonics Corporation). The output of the second delay generator is connected to an "Inhibit" input of the first digital delay generator 166 to permit laser emission only during the second intervals but not during the first intervals or a final data read-out phase.

During an exposure period, an external trigger signal, with a frequency of 1 kHz in this example, triggers row shifting of background spectral signals (empty or null for the first cycle) from a first block of CCD pixels used as storage pixels 44 to a second block of CCD pixels used as detection pixels 42, and Raman spectral signals (empty or null at the start of the first cycle of an exposure period) from the detection pixels 42 to a second block of storage pixels 44 (see FIG. 2d). The block of detection pixels 42 is illuminated by ambient light contributions during the first interval which then follows (see FIG. 2a). The resulting accumulation of charge therefore corresponds to an accumulation of the background spectral signals. Each storage block may be offset from the block of detection pixels 42 for example by about 80 rows, which each storage block being offset in opposite directions from the block of detection pixels for example as illustrated in FIGS. 2a-2d above.

When receiving the following trigger signal, row shifting in the opposite direction of the Raman spectral signals from the second block of storage pixels to the detection pixels, and of the background spectral signals to the first block of storage pixels is triggered and the second interval starts (see also FIG. 2b), with the Raman spectral signals then accumulating, through accumulation of charge, in the detection pixels 42 through illumination by both ambient light conditions, and by laser probe light 22 scattered from the sample for at least some of the second interval (see FIG. 2c).

This cycle of charge shifting and first and second intervals is repeated a large number of times, for example around 2500 times in examples discussed below, which corresponds to a total exposure time (including charge shifting periods between intervals) of about 5 seconds.

At the end of an exposure period, the accumulated charge on the CCD chip (for example operated in an imaging mode with a vertical binning of 16 pixels applied), which represents the background and Raman spectral signals, is read out and digitized. As the illumination conditions for the block of detection pixels can be either with or without laser probe light 22 there exist two different geometries for storage pixels, with either the background spectral signals or the Raman spectral signals being stored in storage blocks further from a readout side of the CCD pixel array. Referring back to the related discussion in respect of FIG. 4, these can be referred to as "a" (laser emission in lower area in final image—see top part of FIG. 4) and "b" (laser emission in upper area in final image—see lower part of FIG. 4). In experimental examples discussed below, spectral signals were always recorded in pairs of exposure periods of "a" and "b" geometries resulting in a total acquisition time of 10 seconds for the combination of the two exposure periods.

In the experimental examples discussed below, the laser driver 164 is set to an injection current of 560 mA, which is below the lasing threshold (corresponding to "laser off" state), and modulated by the first digital delay generator at a frequency of 500 Hz, i.e. firing only during the second intervals of an exposure period when the Raman spectral signals are in the detection pixels. Applying a modulation voltage of 1 V leads to a laser injection current in the "laser on" state of 660 mA resulting in an optical power at the sample position of 52 mW. To avoid laser emission during the row shift periods (which would lead to signal mixing into the background spectral signals), a pulse delay between CCD trigger signal and laser pulse output of 680 μs was applied. Limited by the time available until the subsequent pulse arrives (i.e. 1 millisecond), the laser pulse width was set to 319 μs.

The external trigger signal 64 required by the CCD 40 is provided by the first digital delay generator. It should be noted that the corresponding pulse output is not affected by the "Inhibit" function thus delivering a continuous pulse train to the "EXT TRIG" input of the CCD at the selected frequency of 1 kHz. When an exposure period of multiple cycles of first and second intervals is started in the Solis software, the CCD "Shutter" output 66 will send a trigger signal to the input of the second digital delay generator 168. This delay generator is set to a TTL high configuration so as to activate the "Inhibit" function for the laser output of the first delay generator 166 when no such trigger signal is received, i.e. the laser is in the "off" state. Upon receipt of the trigger signal 66 from the CCD the second delay generator 168 outputs a pulse of selected duration (e.g. 5 seconds) to disable the "Inhibit" function of the first delay generator 166 and consequently enable the laser output for that particular duration. The entire sequence is completed when a pre-set number of cycles of first and second intervals is reached (pre-set in Solis software) and the CCD then undergoes a readout stage of the background and Raman spectral signals.

During this readout phase the CCD may be programmed to bin vertically (along columns) in groups for example of 16 pixels. If each of the blocks of detection pixels and first and second blocks of storage pixels has a height of 64 pixels then this leads to an output from the CCD of four rows of background spectral signals and four rows of Raman spectral signals (one for each sub block of sixteen pixels binned together).

In order to compare experimental results from operating the apparatus of FIG. 7 using the described exposure periods with multiple cycles of first and second intervals (which we will refer to here as "charge shifting mode"), the apparatus was also operated in a more "conventional" mode for comparison. In this conventional mode exposure periods of 50 ms, 100 ms and 500 ms were used. Two adjustment steps were performed to match the illumination conditions in both charge shifting and conventional mode. First, the total amount of ambient light striking the detection pixels during total acquisition time was matched by selecting a suitable number of exposure periods in the conventional read-out mode. Second, for the given number of total exposure periods the total number of laser photons striking the sample during individual exposure periods was matched by selecting an appropriate laser pulse width.

To avoid illumination of the CCD during the read-out phases of conventional mode operation, the timing of the laser pulse was adjusted to be in the centre of each exposure period, i.e. an appropriate laser pulse delay relative to the CCD trigger pulse was chosen. To mimic the read-out conditions of the charge-shifting mode, background and Raman spectral signals were acquired in a multi-track mode using 4 tracks each containing 16 pixels in a column direction. Furthermore, the CCD was externally triggered by the first delay generator 166 to record a series of cycles each with background and then Raman spectral signals corresponding to "laser on" and "laser off" states.

It was noted above that ambient light arriving at the sample may arise from various natural sources such as the sun, and/or various artificial sources such as incandescent, fluorescent, and LED lighting, and may be affected for example by movement of people and objects around the apparatus, movement of the apparatus and/or sample, cloud movements across the sky, lights being turned on and off or otherwise varying in output, and so forth. For the purposes of demonstrating the described apparatus and methods, either a 35 W halogen light bulb (as a broadband light source), or a compact fluorescent light tube (as a narrowband light source), were used to directly illuminate the sample area. Due to its lower intensity the light emitted from a compact fluorescent light tube (having several narrow emission lines) was reflected towards the sample surface using a mirror in addition to the direct illumination of the sample area. Noting the PTFE sample described in relation to FIG. 8 above, the intensity of both ambient lights was set so that the ratio of the main PTFE Raman band at 734 cm$^{-1}$ to the most intense ambient light signal was in the range of 0.008 to 0.026. In a "static illumination condition" the ambient light was used without further physical interference, while under a "dynamic illumination condition" the light intensity was modulated by waving the hand of the operator immediately beneath the corresponding light source crudely mimicking the movement of personal, other objects around the measurement area or the light source itself. For both light sources in "conventional" and "charge-shifting" modes of operation, under "static" and "dynamic" illuminations, 6 repeat sets of experiments were performed with 10 individual sets of background and Raman spectral signals recorded during each experiment.

For the "conventional mode" the spectral signals acquired on four individual tracks corresponding to CCD pixel rows 81-144 were averaged and individual spectra for both cases ("laser on"/"laser off") in the kinetic series were accumulated leading to average spectra, i.e. one containing the PTFE Raman signal and the ambient light signal and the other containing only the ambient light contribution. The minimum values from each of the two spectra were then subtracted, following by normalization to the most intense feature of the ambient light source, i.e. the top of the sharp signal at 1098 cm$^{-1}$ for the fluorescent light (mean of 3 data points) or the top of the broad emission profile between 947 cm$^{-1}$ and 973 cm$^{-1}$ for the incandescent light (mean of 15 data points). Finally, the difference between two corresponding spectra was taken.

The "charge shifting" spectral signals were processed in a similar way as the spectral signals in the "conventional" read-out. However, here intensities acquired in the top (pixel rows 81-144) and bottom (pixel rows 1-64) areas were averaged in the initial step and after difference computation (top area minus bottom area) a final reconstruction step was added by subtracting the "b" spectrum from the "a" spectrum.

To obtain a reference spectrum of the PTFE tape all ambient lights were turned off and two high signal-to-noise-ratio spectra were recorded using an integration time of 10 seconds and 10 individual spectra were averaged each. Subsequently, the spectrum corresponding to the "laser off" state (560 mA injection current) was directly subtracted from the one corresponding to the "laser on" state (660 mA injection current).

From the spectra with contributions from both the PTFE Raman signal and the ambient light the intensities of characteristic spectral features were determined. The PTFE Raman band intensity of the C—F and C—C symmetric stretch band at 734 cm$^{-1}$ was calculated as the average of the intensity of three points at the peak centre above the baseline as determined by the average intensities of 5 points left and right to the band using Microsoft Excel (Microsoft, Redmond, Wash.). The ambient light intensity for the fluorescent light was determined in an identical way but using the most intense emission line at 1098 cm$^{-1}$. In the case of the incandescent light the maximum intensity of the broad emission was calculated by subtracting the average intensity of the background in the range between 70 cm$^{-1}$ and 98 cm$^{-1}$ from the mean intensity in the region between 947 cm$^{-1}$ and 973 cm$^{-1}$. To calculate the PTFE signal-to-noise-ratio (S/N ratio) of the recovered spectra the background noise value was determined in the spectral range from 810 cm$^{-1}$ to 860 cm$^{-1}$ that is free from signals either from PTFE or any of the fluorescent light emission lines.

For quantitative assessment of spectral reconstructions the hit quality index (Hal), as discussed in Rodriguez et al., Anal. Chem. 2011, 83, 4061-4067 (the contents of which are incorporated herein by reference for this particular and all other purposes), was used as indicator of spectral similarity between individual reconstructed spectra and the PTFE reference spectrum. To account for potential variations in the ambient light intensity level, which are inevitable particularly under dynamic illumination conditions, the HQI is plotted against the PTFE signal-to-ambient-light-intensity ratio in FIGS. 9a, 9b, 10a and 10b.

In case of the "conventional" mode the spectral reconstruction was performed simply by scaled subtraction of the "laser off" spectra from the "laser on" spectra. For the "charge-shifting" mode, however, the scaled subtraction of the two separate tracks recorded, i.e. Raman spectral signals (including ambient light) and background spectral signals (ambient light only), left pronounced residuals of the fluorescent light emission lines. The spectral pattern of the residuals resembled the form of a first derivative, indicating that a shift of the ambient light emission lines may have been present during the charge-shifting process. This effect can be understood in terms of the well-known "smile" pattern inherent to imaging spectrographs where the plane grating results in a curved image of the straight entrance slit.

In the "conventional" mode this does not seem to be a problem as the CCD pixel charge is only shifted in one direction, i.e. during the actual read-out phase (duration about 90 milliseconds per exposure). Therefore, consecutive spectra recorded with and without the laser being turned on experience exactly the same amount of distortion and the individual contributions cancel out during subtraction. In the "charge-shifting" mode, however, the charge is shifted in both directions during the exposure phase and due to the relatively large number of 80 shifted rows the distortions caused by the "smile" effect cannot fully be compensated. It should be noted that the effect is small in relative terms as the maximum residual intensity around 1100 cm$^{-1}$ only amounts to less than 6% of the original intensity of the fluorescent light emission line in the top and bottom track spectra.

Nevertheless, using the technique discussed above in respect of FIG. 4 is helpful to overcome this distortion. Determined by the starting trigger signal, the Raman scattered light originating from the PTFE sample was either imaged on the top track ("a" spectrum) or on the bottom track ("b" spectrum) in "charge-shifting" mode. Subtracting the bottom from the top track in both cases resulted in a positive Raman intensity for the "a" differences while for the "b" difference a negative Raman intensity was obtained. As the spectral distortions are equal in both cases they are effectively eliminated by subtracting both difference spectra from each other leading to the reconstructed PTFE spectrum. In the presently described experiments, a comparison of the reconstructed spectrum with the reference spectrum highlights the high quality of the obtained spectrum with only very minor residual distortions being left.

The average reconstructed spectra under "static" illumination conditions showed very similar patterns in "conventional" and "charge-shifting" mode. The fluorescent light interference was effectively removed in all cases with only minor contributions from the formerly very intense emission lines remaining and a good reproducibility of reconstructed spectra being achieved (as indicated by the standard deviation). Regarding the S/N ratios of the reconstructed spectra, however, there were distinct differences between individual acquisition times in conventional read-out and the charge-shifting modes. In the case of an interfering light source with mainly sharp and intense emission lines on top of an almost flat background this effect can be explained in terms of read-out noise dependent on the number of individual acquisitions. While in "charge-shifting" mode only two read-outs took place, the number of read-out cycles is 18, 74 and 122 for sub-acquisition times of 500, 100 and 50 milliseconds in "conventional" mode, respectively. At 500 millisecond acquisition time, due to the relatively low number of acquisitions, the detrimental effect of accumulated read-out-noise vanishes as obtained S/N ratios are identical to the "charge-shifting" mode.

Under "dynamic" illumination conditions the standard deviation of reconstructed spectra was much larger for the "conventional" read-out mode compared to the "charge-shifting" mode. Particularly in the case of a sub-acquisition time of 100 milliseconds the residuals of fluorescent light emission lines were prominent. Further tests showed that this observation is due to the relatively large active surface of the fluorescent light bulb (2 separate U-shaped discharge tubes with 10 mm diameter and 94 mm length each) resulting in a spatial variation of the spectral emission profile. When moving the hand between light source and experimental setup under dynamic illumination conditions the collection optics captured slightly different spectral distribution at different times. As the hand movement was not synchronized with the CCD read-out frequency the spectral distortions are not evenly distributed onto adjacent spectra in the kinetic series. Consequently, the spectral reconstruction process was not capable of removing these distortions effectively. At the applied hand waving frequency sub-acquisition times of 50 milliseconds and 500 milliseconds resulted in better reconstruction performance but it should be noted that this may not be the case for different modulation frequencies. The only way to overcome this fundamental issue is the ability of the "charge-shifting" mode operated for example at a frequency of 1 kHz to effectively distribute fast variations in the background level evenly between the first and second intervals of the exposure period so that subsequent spectral reconstruction can efficiently remove these disturbances. Due to the lower absolute intensity of fluorescent light striking the CCD the S/N ratios increase in all cases but still show the same trend already observed for the "static" illumination conditions.

Figure 9A:
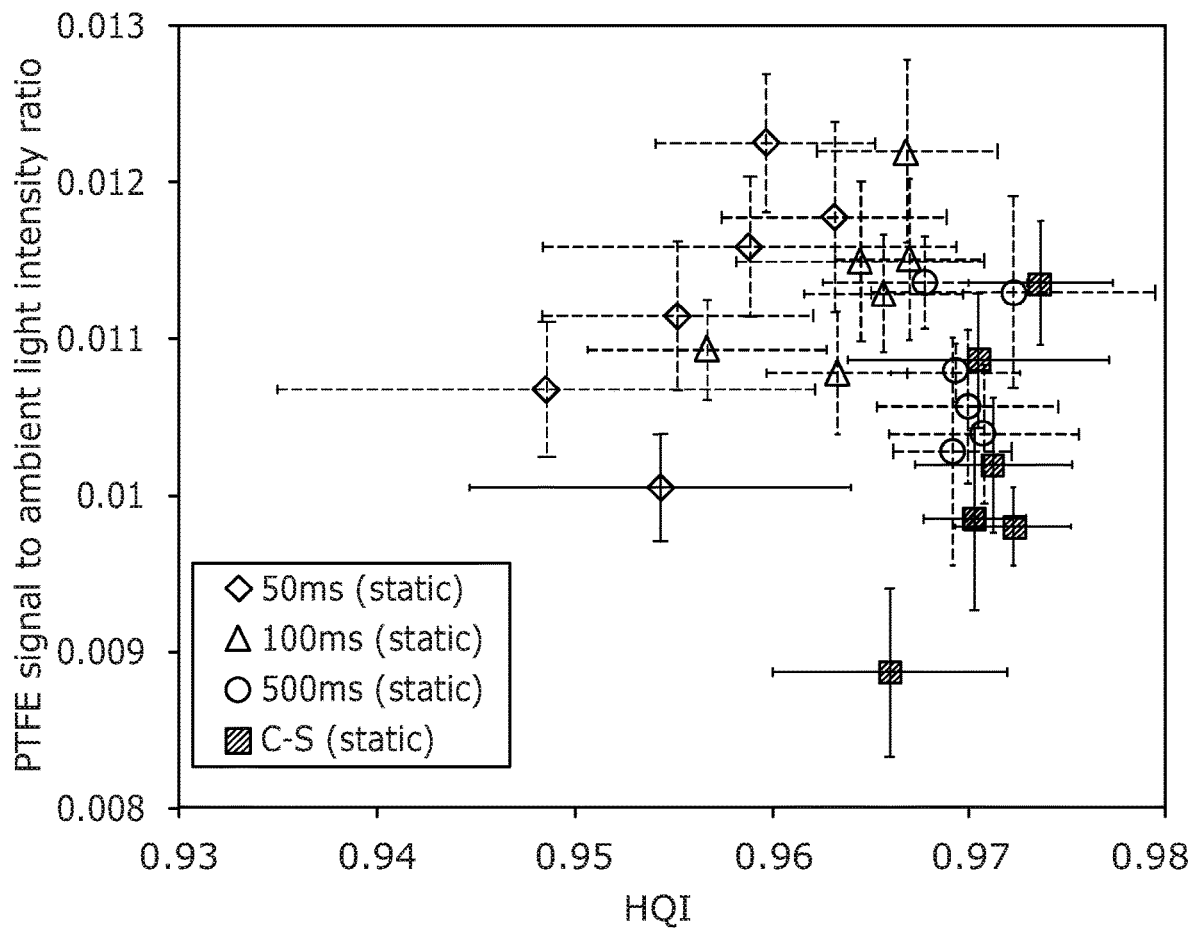
FIGS. 9a and 9b show HQI spectral matching quality indicators (abscissa) against Raman signal to ambient light intensity ratio of a PTFE sample, for various "conventional" modes of operation of the CCD at 50, 100 and 500 millisecond exposure periods, as well as using the "charge-shifting" technique of the present invention (C-S).
Figure 9B:
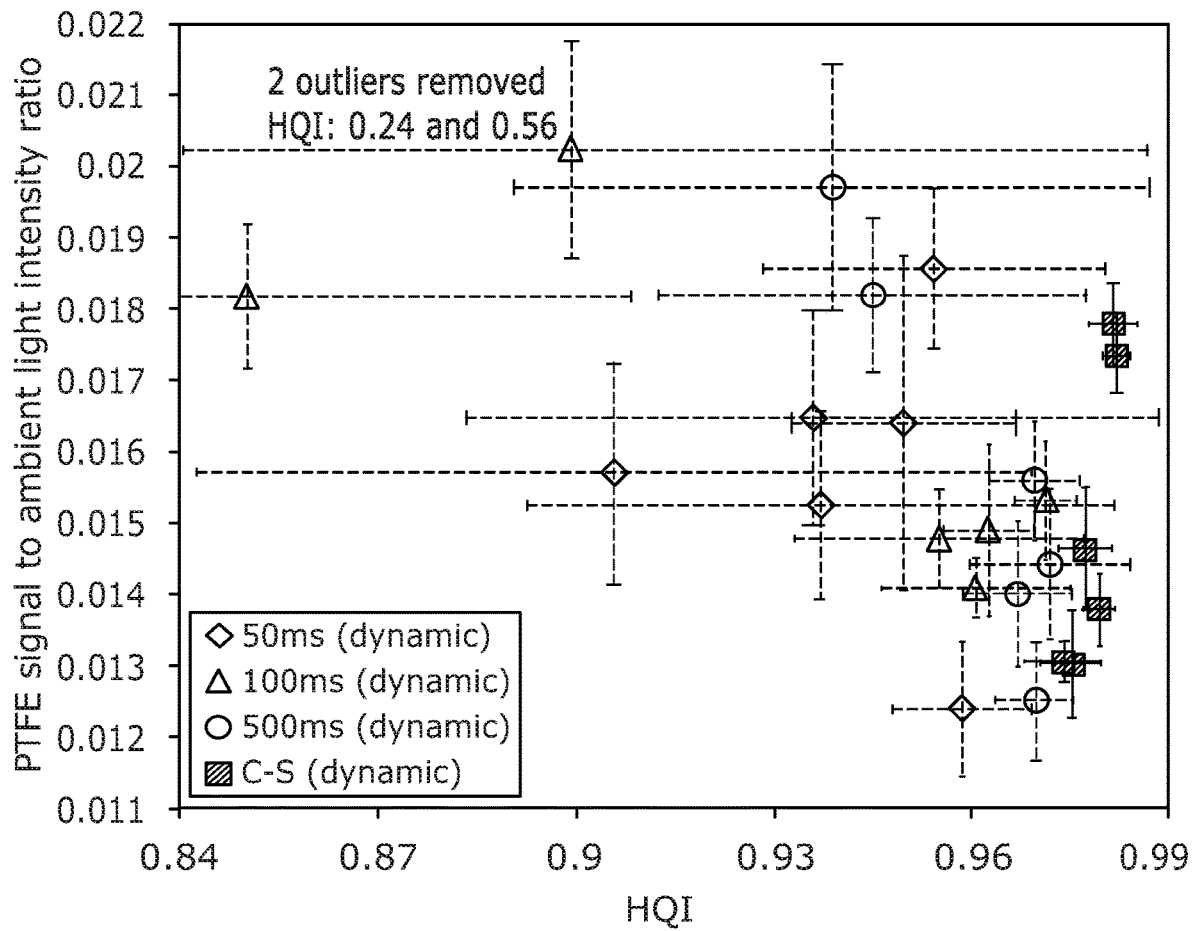

For a quantitative assessment of the recovered spectra in "conventional" and "charge-shifting" modes the PTFE to fluorescent light intensity ratios are plotted in FIGS. 9a and 9b against the hit quality index (HQI) with a perfect spectral match corresponding to a HQI of one.

Under the "static" illumination conditions of FIG. 9a there is not much difference in reconstruction performance between the "conventional" and the "charge-shifting" modes with very good reconstructions being achieved. For the "conventional" read-out, however, there is a trend for better reconstructions with increased sub-acquisition time. The spectra reconstructed from the series of 18 individual spectra recorded at 500 milliseconds show the best performance and are, at comparable PTFE signal to ambient light intensity ratios, virtually identical to the spectra reconstructed from the "charge-shifting" mode. As there is no significant amount of shot-noise added to the spectra by means of the fluorescent light emission with its almost flat baseline this effect can be understood in terms of increased amounts of accumulated read-out noise for shorter sub-acquisition times. As expected for non-varying backgrounds, the "conventional" mode at frequencies in the range of 1.7-7.5 Hz is capable of rejecting those static contributions effectively.

FIG. 9b shows that in the case of "dynamic" illumination, however, the "charge-shifting" mode is superior in addressing rapidly varying modulations of ambient light interference resulting in the best reconstruction (highest HQI) and the best reproducibility (lowest standard deviation within each set of 10 spectra). It should be noted that the reconstruction of two spectra recorded at 100 millisecond exposure time under "conventional" conditions led to very poor outcomes and that those outliers have been removed for clarity of presentation. The results demonstrate that the "conventional" mode which is limited to frequencies of less than 10 Hz (due to inevitable read-out phases between individual acquisitions) is not able to efficiently and reproducibly address irregular modulations/variations of ambient light interference. In terms of material identification a typical minimal HQI used for confirmation purposes is 0.95 (see the Rodriguez et al., reference above). Applying this threshold value the correct classification rates for the PTFE sample under investigation were 57%, 68% and 82% for the "conventional" mode with sub-acquisition times of 50, 100 and 500 milliseconds, respectively. In contrast, the superior spectral reconstruction performance of the "charge-shifting" mode led to 100% correct classification rate, i.e. the sample was identified as PTFE in 60 out of 60 cases.

One major difference between the two modes is that the reconstruction performance decreases from "static" to "dynamic" illumination conditions for all investigated sub-acquisition times in conventional mode (reductions of 1.0-3.2%) while the opposite is the case for the charge-shifting mode (increase by 0.8%). Furthermore, the reproducibility of spectral reconstructions is reduced in the "conventional" mode by factors of 4.3, 12.2 and 5.4 for sub-acquisition times of 50, 100 and 500 milliseconds, respectively while no change is observed for the "charge-shifting" mode. This behaviour can be explained by two counteracting effects. In the "static" illumination the accumulated fluorescent light intensity during the measurement is higher (but stable) whereas under "dynamic" illumination conditions a varying (but overall lower) amount of ambient light is captured. As the "charge-shifting" mode (in this case operated at 1 kHz) has a superior ability to deal with modulated backgrounds, the smaller absolute fluorescent light intensity leads to a better spectral reconstruction under "dynamic" illumination conditions. In contrast, the "conventional" mode is not able to handle background variations that well so in this case the benefit of lower absolute intensities cannot be exploited leading to decreased reconstruction performance and increased variation.

The incandescent light source had a broad and intense spectral emission adding a significant background to the recorded spectra. The reconstructed spectra under "static" illumination conditions consequently showed S/N ratios about one order of magnitude lower compared to the fluorescent light of comparable peak intensity. In contrast to the fluorescent light in this case there was no trend observable for the S/N ratios with respect to the sub-acquisition times in "conventional" mode. Owing to the spectral properties of the incandescent light the amount of photon shot noise contained in the spectra was much larger than the accumulated read-out noise and can therefore be considered as dominant source of noise.

Under "dynamic" illumination conditions spectral distortions introduced by the modulation of the light intensity contribute as a further source of variation. In the "conventional" mode this effect caused the standard deviation to increase in the low and high wavenumber regions (i.e. outside the region where normalization is performed for the spectral reconstruction) relative to static illumination due to the limited ability of this configuration to deal with varying backgrounds. For the "charge-shifting" mode, however, the ability to effectively reject that type of variation led to a significantly reduced standard deviation as the overall light intensity was reduced compared to the "static" illumination conditions. Regarding the S/N ratios governed by fine pixel-to-pixel noise there was no difference observable between the various modes of operation. The absolute values, however, were increased by factors of about 1.4-1.6 compared to the "static" illumination conditions as the overall incandescent light intensity was reduced resulting in a lower shot noise contribution.

Figure 10A:
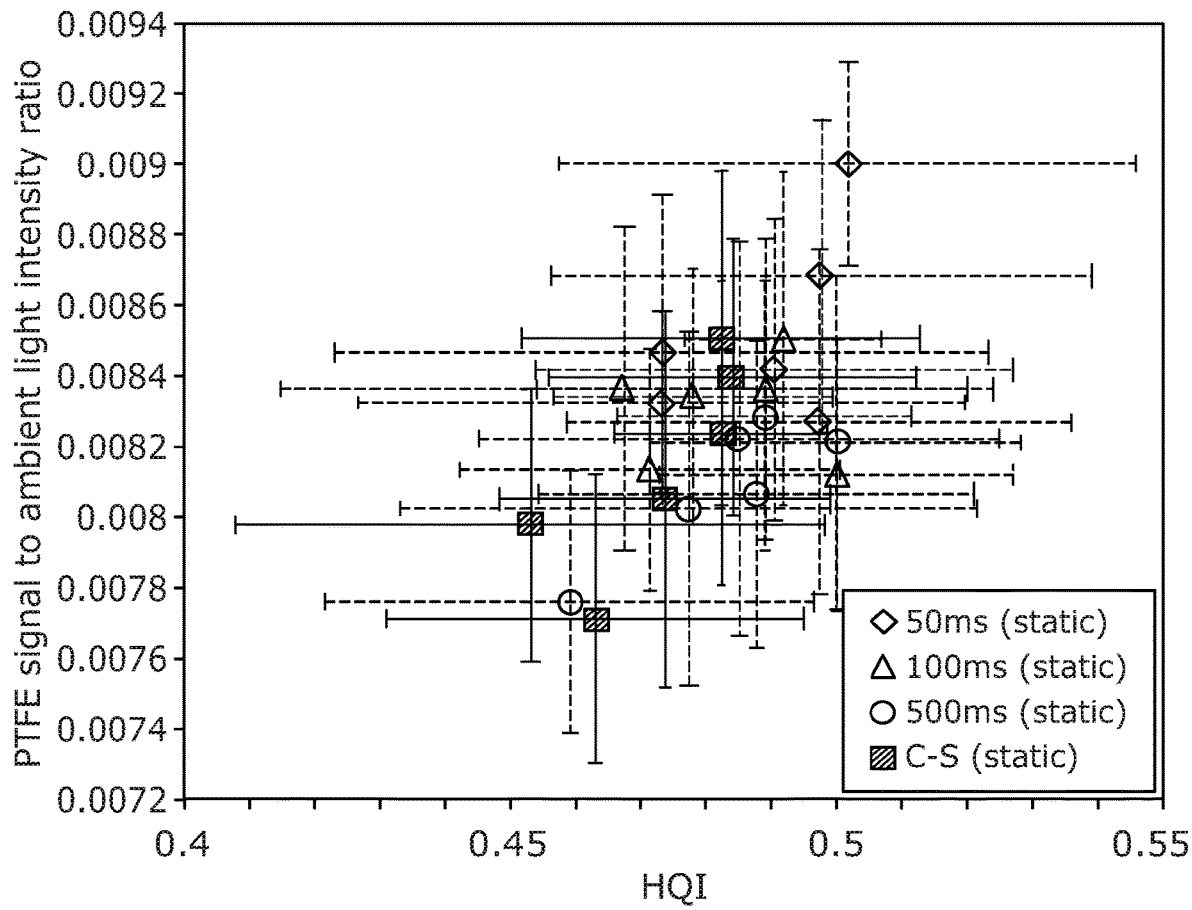
FIGS. 10a and 10b provide results corresponding to those of FIGS. 9a and 9b, but with the ambient light provided by an incandescent bulb.

FIG. 10a presents the PTFE signal to incandescent light intensity ratio under "static" illumination conditions. In this configuration all reconstructed spectra are identical within error margins highlighting that the "charge-shifting" mode performs equally well compared to the "conventional" mode at any of the selected sub-acquisition times. Due to the large amount of shot noise being present in the spectra the absolute values for the HQI are clearly reduced (HQI=0.40-0.55) compared to the fluorescent light interference (HQI=0.94-0.98).

Figure 10B:
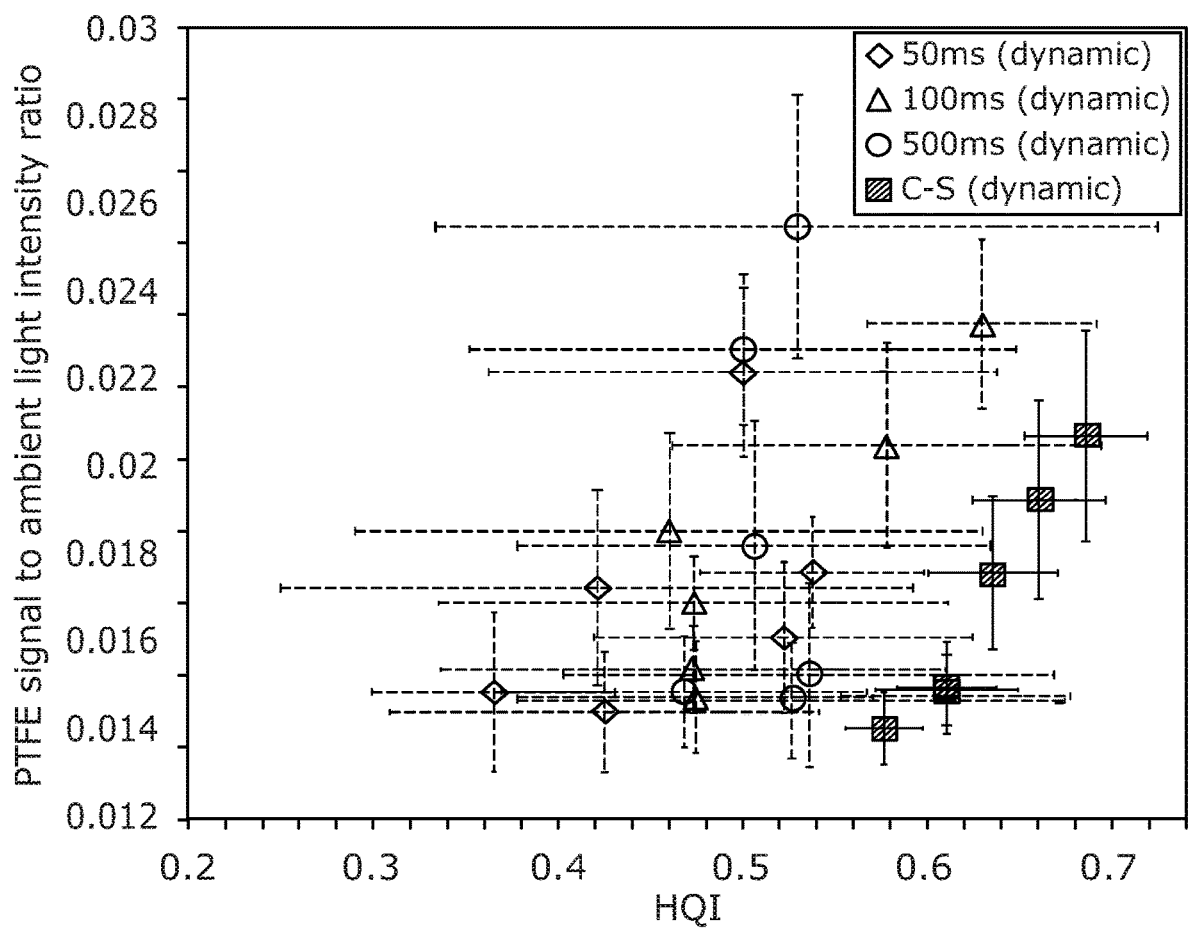

Under "dynamic" illumination conditions the "charge-shifting" method demonstrates its ability for the efficient rejection of varying backgrounds resulting in the best spectral reconstruction and lowest variability in this case, as seen in FIG. 10b. Independent of the chosen sub-acquisition time the spectral reconstruction performance for the "conventional" mode is inferior and shows a larger variation due to residual distortions still being present after spectral reconstruction. Particularly for the "charge-shifting" mode spectra it becomes evident that there is a direct proportionality between achieved HQI and PTFE signal to incandescent light intensity ratio. This effect is expected as better spectral matches can be realized when the contribution of shot noise is reduced.

In contrast to the spectrally narrow distortions introduced by the fluorescent light source the variations in the reconstructed spectra caused by the incandescent light can be regarded as spectrally broad modulations of the signal background. For the "conventional" mode an attempt has therefore been made to remove the spectrally slowly varying baseline by a 7th order polynomial fitting (MATLAB R2013a). Subsequently the spectral reconstruction performance of the corrected spectra was evaluated by means of the HQI. While spectral reconstruction of the distorted spectra (recorded in "conventional" mode under "dynamic" illumination) show decreased performance and reproducibility compared to the "charge-shifting" mode, this difference vanishes after polynomial baseline correction. While this approach seems to be successful for a sample with sharp and well-separated Raman bands (as PTFE in this case) it should be noted that in the case of more challenging specimens, e.g. biological tissue, there is a risk of adding significant artefacts to the spectra by means of the polynomial fitting.

Table 1 presents a comparison of "conventional" and "charge-shifting" modes in terms of the file size and measurement time required for one acquisition, corresponding to one exposure period in the charge-shifting mode. To address fast variations in ambient light intensities it may be beneficial to use the fastest available CCD modulation frequency. For the "conventional" mode this is 7.5 Hz for 50 millisecond sub-acquisition time, whereas in the "charge-shifting" mode the achievable frequency of 1 kHz is two orders of magnitude faster and thus provides a clear advantage. As the removal of ambient light interference is particularly required outside the usual laboratory environment, i.e. where portable instrumentation will be applied, care should also be taken with respect to the amount of data generated as data storage capacity may be limited.

TABLE 1

| Acquisition mode | Average file size for fluorescent light/kB | Average file size for incandescent light/kB | Total acquisition time per spectrum/s |
|---|---|---|---|
| 50 ms conven. | 2680 | 3068 | 16.3 |
| 100 ms conven. | 1627 | 1890 | 13.7 |
| 500 ms conven. | 401 | 466 | 10.6 |
| Charge-shifting | 149 | 180 | 10.0 |

As shown in Table 1 the data file sizes, for the combined background and Raman spectral signals as read from the CCD, vary with the total amount of ambient light striking the CCD. Overall, the original file sizes in "conventional" mode, as obtained from the CCD software, is larger by factors of up to 18 (for 7.5 Hz operation) as compared to the "charge-shifting" mode. Taking the incandescent light as an example, the total file size for 50 spectra would amount to 153.4 MB for the "conventional" mode at a frequency of 7.5 Hz but only 9.0 MB in the "charge-shifting" mode. A main limitation of the "conventional" mode is therefore that fast variations in the ambient light can only be compensated for in kinetic mode but this requires each single sub-acquisition of the kinetic series to be read-out and stored. As access to each individual sub-acquisition is not required in most cases, the "charge-shifting" technique is beneficial in this respect by limiting the data to the amount required for spectral reconstruction.

Finally, not only the data volume generated but also the time required to complete the measurements is an important factor. From Table 1 it can be seen that, in comparison with the "charge-shifting" mode, the conventional mode is slower by 63%, 37% and 6% for 50 millisecond, 100 millisecond and 500 millisecond, respectively. Taking the acquisition of 50 spectra as an example again, this would take 13:35 minutes in "conventional" mode at 7.5 Hz but only 8:20 minutes using the "charge-shifting" technique. The measurement times can be reduced by applying a lower frequency in "conventional" mode but this will be at the expense of not being able to account for fast variations in the ambient light in an effective way anymore.

Although particular embodiments and applications of the invention have been described, it will be apparent to the skilled person that various modifications and alterations can be made without departing from the scope of the invention.

For example, the described techniques may be used to implement time resolved Raman spectroscopy, by determining compensated Raman spectral signals in respect of a sample at multiple consecutive time frames which could for example be at intervals of the order of between one tenth of a second and one second apart from each other. The described techniques could also be used for Raman imaging, or wide field Raman imaging, in which Raman spectral features such as individual Raman bands are detected across an image plane.

The invention claimed is:

1. A method of measuring Raman spectral features of a sample onto which ambient light is incident, comprising:

defining, on a charge coupled device (CCD) having a plurality of pixels, detection pixels, and storage pixels separate from the detection pixels;

providing a laser light source arranged to direct laser probe light to the sample;

providing collection optics arranged to direct light scattered from the sample to the detection pixels;

for the duration of an exposure period, repeating a cycle of at least a first interval during which background light from the sample, but not laser probe light, is received at the detection pixels for the accumulation of first, background, spectral signals at those pixels, and a second interval during which both background light from the sample and laser probe light Raman scattered by the sample is received at the detection pixels for the accumulation of second, Raman, spectral signals at those pixels;

during the first intervals, further accumulating the first, background, spectral signals in the detection pixels, while storing the accumulated second, Raman, spectral signals in said storage pixels;

during the second intervals, further accumulating the second, Raman, spectral signals in the detection pixels, while storing the accumulated first, background, spectral signals in said storage pixels, wherein the background light from the sample comprises ambient light scattered by the sample.

2. The method of claim 1 wherein the laser probe light is incident on the sample during each second interval and is absent from the sample during each first interval.

3. The method of claim 2 wherein the laser light source is operated to emit said laser probe light only during each said second interval, and not during each first interval.

4. A method of measuring Raman spectral features of a sample, comprising:

defining, on a charge coupled device (CCD) having a plurality of pixels, detection pixels, and storage pixels separate from the detection pixels;

providing a laser light source arranged to direct laser probe light of multiple different wavelengths to the sample;

providing collection optics arranged to direct light scattered from the sample to the detection pixels;

for the duration of an exposure period, repeating a cycle of at least a first interval during which both background light from the sample, and laser probe light of a first wavelength scattered by the sample, are received at the detection pixels for the accumulation of first, Raman, spectral signals at those pixels, and a second interval during which both background light from the sample, and laser probe light of a second wavelength scattered by the sample, the second wavelength being different to the first wavelength, are received at the detection pixels for the accumulation of second, Raman, spectral signals at those pixels;

during the first intervals, further accumulating the first, Raman, spectral signals in the detection pixels, while storing the accumulated second, Raman, spectral signals in said storage pixels;

during the second intervals, further accumulating the second, Raman, spectral signals in the detection pixels, while storing the accumulated first, Raman, spectral signals in said storage pixels.

5. The method of claim 4 wherein the cycle further comprises at least a third interval during which both background light from the sample, and laser probe light of a third wavelength scattered by the sample, are received at the detection pixels for the accumulation of third, Raman, spectral signals at those pixels, the method further comprising:
during the first and second intervals, storing the accumulated third, Raman, spectral signals in the storage pixels; and
during the third intervals, further accumulating the third, Raman, spectral signals in the detection pixels, while storing the accumulated first and second, Raman, spectral signals in the storage pixels.

6. The method of claim 4 wherein:
the cycle further comprises at least a further interval during which background light from the sample, but not laser probe light scattered by the sample, is received at the detection pixels for the accumulation of further, background spectral signals at those pixels, the method further comprising:
during the first and second intervals, storing the accumulated further, background spectral signals in the storage pixels; and
during the further intervals, further accumulating the further, background spectral signals in the detection pixels, while storing the accumulated first and second, Raman, spectral signals in the storage pixels.

7. The method of claim 4 wherein the background light from the sample which is received during intervals when scattered laser probe light is also received from the sample comprises fluorescence of the sample.

8. The method of claim 4 wherein the fluorescence of the sample is emitted responsive to the laser probe light incident on the sample.

9. The method of claim 4 wherein the background light from the sample comprises ambient light incident on and scattered by the sample.

10. The method of claim 4 further comprising:
after the exposure period, reading from the CCD the spectral signals accumulated during the exposure period; and
calculating compensated Raman spectral signals, compensated to remove signals of the background light, using the read accumulated spectral signals from one or more such exposure periods.

11. The method of claim 10 further comprising determining a chemical characteristic of the sample from the compensated Raman spectral signals from one or more exposure periods.

12. The method of claim 4 wherein the collection optics comprises a spectrometer arranged to spectrally disperse the light scattered from the sample across the detection pixels.

13. The method of claim 4 wherein the method is carried out by a hand held device.

14. The method of claim 4 wherein the repeated cycle further comprises a further interval during which laser probe light scattered by a reference sample is received at the detection pixels for the accumulation of reference spectral signals.

15. The method of claim 4, wherein the spectral signals are moved between the detection pixels and the storage pixels by row shifting charge contents of the pixels of the CCD.

16. The method of claim 4 wherein the storage pixels comprise at least first and second groups of storage pixels disposed on opposing sides of the detection pixels, the first group being used for storage of the accumulated first, background or Raman, spectral signals, and the second group being used for storage of the accumulated second, Raman, signals.

17. The method of claim 4 wherein:
the storage pixels comprise at least first and second groups of storage pixels disposed on opposing sides of the detection pixels;
during a first exposure period using the first group for storage of the accumulated first, background or Raman, spectral signals, and using the second group for storage of the accumulated second, Raman, spectral signals;
during a second exposure period using the first group for storage of the accumulated second, Raman, spectral signals, and using the second group for storage of the accumulated first, background, spectral signals.

18. The method of claim 17 comprising:
reading the accumulated first and second spectral signals from the CCD at the end of each of the first and second exposure periods;
combining together the accumulated first spectral signals from both exposure periods;
combining together the accumulated second spectral signals from both exposure periods; and
calculating compensated Raman spectral signals, compensated to remove signals of the background light, using the combined first and second spectral signals from both exposure periods.

19. The method of claim 4 wherein the storage pixels comprise rows or blocks of pixels interleaved between rows or blocks of the detection pixels.

20. The method of claim 4 wherein the collection optics comprises masking arranged to block light scattered from the sample from being received at the storage pixels.

21. The method of claim 4 wherein the exposure period comprises at least 10, or at least 100, of each of the first and second intervals.

22. The method of claim 4 wherein the exposure period has a duration of at least 1 second.

23. The method of claim 4 wherein the laser light source is arranged to direct the laser probe light to an illumination region on a surface of the sample, and the collection optics are arranged to collect light scattered from a collection region on the sample surface for receiving at the detection pixels, the collection region being spatially offset from the illumination region.

24. The method of claim 23 comprising accumulating both first, background or Raman, spectral signals and second, Raman, spectral signals, during each of a plurality of exposure periods, a spatial offset between said illumination and collection regions being different for each of the exposure periods.

25. The method of claim 24 further comprising determining a chemical characteristic for one or more subsurface regions of the sample by associating the spectral signals for each offset with a different depth or distribution of depth within the sample.

26. Apparatus for detecting Raman spectral features of a sample under conditions of variable ambient light, comprising:
a charge coupled device (CCD) having a plurality of pixels, the pixels comprising detection pixels and storage pixels;
a laser light source arranged to direct laser probe light to the sample;
collection optics arranged to direct light scattered from the sample to the detection pixels;
a controller arranged to implement an exposure period during which are interleaved a plurality of first intervals when background light from the sample, but not laser probe light, is received at the detection pixels for the accumulation of first, background, spectral signals at those pixels, and a plurality of second intervals during which both background light from the sample and laser probe light scattered by the sample is received at the detection pixels for the accumulation of second, Raman, spectral signals at those pixels, such that during each first interval, the first, background, spectral signals are further accumulated in the detection pixels, while storing the accumulated second, Raman, spectral signals in said storage pixels, and such that during each second interval, the second, Raman, spectral signals are further accumulated in the detection pixels, while storing the accumulated first, background, spectral signals in said storage pixels, wherein the background light from the sample comprises ambient light scattered by the sample.

27. The apparatus of claim 26 arranged such that the laser probe light is incident on the sample during each second interval and is absent from the sample during each first interval.

28. The apparatus of claim 26 arranged such that the laser light source emits the laser probe light during the second intervals, but not during the first intervals.

29. Apparatus for detecting Raman spectral features of a sample, comprising:
a charge coupled device (CCD) having a plurality of pixels, the pixels comprising detection pixels and storage pixels;
a laser light source arranged to direct laser probe light of either a first or a second wavelength to the sample;
collection optics arranged to direct light scattered from the sample to the detection pixels;
a controller arranged to implement an exposure period during which are interleaved a plurality of first intervals during when both background light from the sample, and laser probe light of the first wavelength scattered by the sample, are received at the detection pixels for the accumulation of first, Raman, spectral signals at those pixels, and a plurality of second intervals during which both background light from the sample and laser probe light of the second wavelength scattered by the sample are received at the detection pixels for the accumulation of second, Raman, spectral signals at those pixels;

such that during the first intervals, the first, Raman spectral signals are further accumulated in the detection pixels, while the accumulated second, Raman spectral signals are stored in said storage pixels; and such that during the second intervals, the second, Raman, spectral signals are further accumulated in the detection pixels, while storing the accumulated first, Raman, spectral signals in said storage pixels.

30. The apparatus of claim 29 wherein the background light from the sample comprises fluorescence of the sample.

31. The apparatus of claim 29 wherein the fluorescence of the sample is emitted responsive to the laser probe light incident on the sample.

32. The apparatus of claim 29 wherein the background light from the sample comprises ambient light incident on and scattered by the sample.

33. The apparatus of claim 29 arranged such that the laser light source emits laser probe light of the first wavelength during the first intervals, and emits laser probe light of the second wavelength during the second intervals.

34. The apparatus of claim 29 further comprising an analyser arranged to receive from the CCD, after the exposure period, the first, background or Raman, spectral signals and the second, Raman, spectral signals accumulated during the exposure period, and to calculate compensated Raman spectral signals, compensated to remove signals of the background light, from the first and second spectral signals.

35. The apparatus of claim 34 wherein the analyser is arranged to output a chemical characteristic of the sample determined from the compensated Raman spectral signals.

36. The apparatus of claim 29 wherein the collection optics comprises a spectrometer arranged to spectrally disperse the light scattered from the sample across the detection pixels.

37. The apparatus of claim 29 wherein the apparatus is comprised in a hand held analysis device.

38. The method of claim 1, further comprising:
after the exposure period, reading from the CCD the spectral signals accumulated during the exposure period; and
calculating compensated Raman spectral signals, compensated to remove signals of the background light, using the read accumulated spectral signals from one or more such exposure periods.

39. The method of claim 1 wherein the collection optics comprises a spectrometer arranged to spectrally disperse the light scattered from the sample across the detection pixels.

40. The method of claim 1, wherein the spectral signals are moved between the detection pixels and the storage pixels by row shifting charge contents of the pixels of the CCD.

41. The method of claim 1 wherein the storage pixels comprise at least first and second groups of storage pixels disposed on opposing sides of the detection pixels, the first group being used for storage of the accumulated first, background or Raman, spectral signals, and the second group being used for storage of the accumulated second, Raman, signals.

42. The apparatus of claim 26 further comprising an analyser arranged to receive from the CCD, after the exposure period, the first, background or Raman, spectral signals and the second, Raman, spectral signals accumulated during the exposure period, and to calculate compensated Raman spectral signals, compensated to remove signals of the background light, from the first and second spectral signals.

43. The apparatus of claim 26 wherein the collection optics comprises a spectrometer arranged to spectrally disperse the light scattered from the sample across the detection pixels.

* * * * *

UNITED STATES PATENT AND TRADEMARK OFFICE
CERTIFICATE OF CORRECTION

PATENT NO. : 11,300,451 B2
APPLICATION NO. : 17/282438
DATED : April 12, 2022
INVENTOR(S) : Pavel Matousek, Kay Sowoidnich and Michael Towrie It is certified that error appears in the above-identified patent and that said Letters Patent is hereby corrected as shown below:

On the Title Page

Item (71) Applicant:
Please insert --Wiltshire-- after "Swindon"

Item (73) Assignee:
Please insert --Wiltshire-- after "Swindon"

Signed and Sealed this
Twenty-ninth Day of November, 2022

*Katherine Kelly Vidal*

Katherine Kelly Vidal
*Director of the United States Patent and Trademark Office*